United States Patent [19]

Hamanaka et al.

[11] Patent Number: 5,344,836
[45] Date of Patent: Sep. 6, 1994

[54] FUSED BENZENEOXYACETIC ACID DERIVATIVES

[75] Inventors: Nobuyuki Hamanaka; Kanji Takahashi; Hidekado Tokumoto, all of Osaka, Japan

[73] Assignee: Ono Pharmaceutical Co., Ltd., Osaka, Japan

[21] Appl. No.: 971,581

[22] Filed: Nov. 5, 1992

[30] Foreign Application Priority Data

Nov. 11, 1991 [JP] Japan .................. 3-322612
Jul. 3, 1992 [JP] Japan .................. 4-220246

[51] Int. Cl.$^5$ .................. A61K 31/44; C07D 213/02
[52] U.S. Cl. .................. 514/332; 514/357; 514/428; 514/534; 514/563; 546/265; 546/336; 548/561; 560/42; 562/451; 562/457
[58] Field of Search .................. 560/37, 42; 562/451, 562/457; 514/332, 357, 428, 534, 563; 546/265, 336; 548/561

[56] References Cited

FOREIGN PATENT DOCUMENTS

| | | | |
|---|---|---|---|
| 0013607 | 7/1980 | European Pat. Off. | 560/37 |
| 0043292 | 1/1982 | European Pat. Off. | 560/37 |
| 0135177 | 3/1985 | European Pat. Off. | 560/37 |
| 3504677 | 8/1986 | European Pat. Off. | 560/37 |
| 0270929 | 6/1988 | European Pat. Off. | 560/37 |

OTHER PUBLICATIONS

Nature, vol. 263, Oct. 21, 1976, pp. 663–665.
Prostaglandins, vol. 12, No. 5, Nov. 1976, pp. 685–713.
Prostaglandins, vol. 12, No. 6, Dec. 1976, pp. 915–928.
Prostaglandins, vol. 13, No. 3, Mar. 1977, pp. 375–388.
Chemical & Engineering News, Dec. 20, 1976, pp. 17–19.
Br. J. Pharmac. 76, 1982, pp. 423–438.
Br. J. Pharmac. 84, 1985, pp. 595–607.
Br. J. Pharmac. 102, 1991, pp. 251–265.

Primary Examiner—C. Warren Ivy
Assistant Examiner—Zinna N. Davis
Attorney, Agent, or Firm—Sughrue, Mion, Zinn, Macpeak & Seas

[57] ABSTRACT

A fused benzenoxyacetic acid derivative of the formula (I):

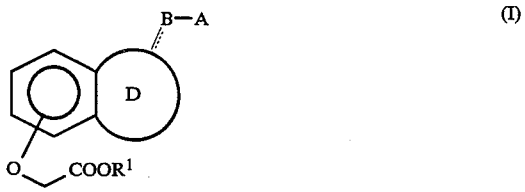

and salts thereof possess an agonistic on PGI$_2$ receptor, so it is useful for prevention and/or treatment of thrombosis, arteriosclerosis, ischemic heart diseases, gastric ulcer and hypertention.

18 Claims, No Drawings

FUSED BENZENEOXYACETIC ACID DERIVATIVES

SUMMARY

This invention is related to fused benzeneoxyacetic acid derivatives.

More particularly, this invention is related to:

1) fused benzeneoxyacetic acid derivatives of the formula (I):

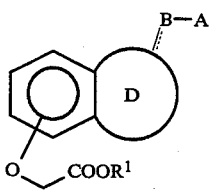

wherein all the symbols are the same meaning as hereafter defined, and non-toxic salts thereof and non-toxic acid addition salts thereof, 2) processes for the preparation thereof, and 3) pharmaceutical agents containing them as active ingredient.

BACKGROUND OF THE INVENTION $PGI_2$ is a physiologically active natural substance having the following structural formula, which is biosynthesized from $PGH_2$ in the metabolic process in vivo called arachidonate cascade.

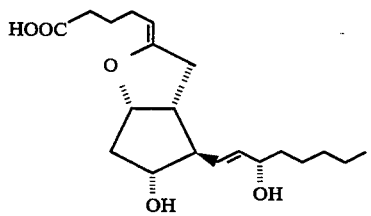

(see Nature, 263, 663(1976), Prostaglandins, 12, 685(1976), ibid, 12, 915(1976), ibid, 13, 375(1977) and Chemical and Engineering News, Dec. 20, 17(1976).

$PGI_2$ has been confirmed to possess not only a very strong inhibitory activity on blood platelet aggregation but a dissociative activity on blood platelet aggregation, an inhibitory activity on blood platelet adhesion, a vasodilating activity, an inhibitory activity on gastric acid secretion etc. Therefore, it has been considered that $PGI_2$ is useful for the prevention and/or the treatment for thrombosis, arteriosclerosis, ischemic heart diseases, gastric ulcer, hypertension etc. But its application for pharmaceuticals is limited because of its chemical instability and difficulty of separation of the actions according to purpose. Accordingly, various $PGI_2$ derivatives have been synthesized and many researches have been carried out for the maintenance and the separation of the actions. However, we have not necessarily satisfactory results yet.

Recently, in order to solve two problems above described, the research for $PGI_2$ receptor agonists which have a new-typed skeleton and may be useful for the treatment of or for the prevention of the above diseases, in view of $PGI_2$ receptor level, has been carried out.

RELATED ARTS

It has been reported in the literatures, that the following compounds not having the $PGI_2$ skeleton are $PGI_2$ receptor agonists which bind to a $PGI_2$ receptor and inhibit blood platelet aggregation:

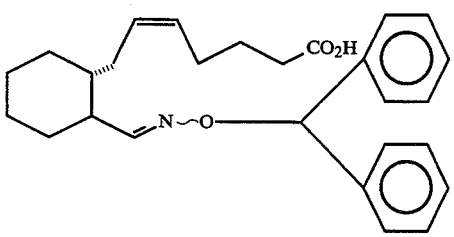

(see Brit. J. Pharmacol., 76, 423(1982), ibid, 84, 595(1985), and the Japanese Patent Kohyo No. 55-501098),

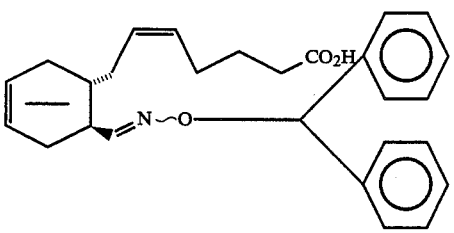

(see Brit. J. Pharmacol., 76, 423(1982), ibid, 84, 595(1985), and the Japanese Patent Kohyo No. 57-501127), and

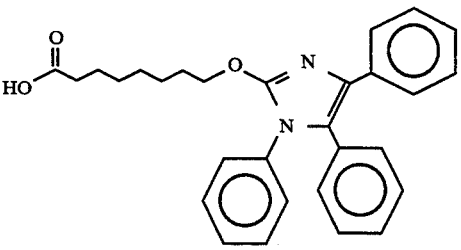

(see Brit. J. Pharmacol., 102, 251-266)(1991) and the West German Patent Publication No. 3,504,677).

PURPOSE OF THE INVENTION

Energetic investigations have been carried out in order to discover new $PGI_2$ receptor agonists having a skeleton in chemical structure different from the compounds mentioned above, the present inventors have found that a kind of fused benzeneoxyacetic acid derivatives has an activity on binding to $PGI_2$ receptor and an inhibitory activity on blood platelet aggregation, and have accomplished the present invention.

The fused benzeneoxyacetic acid derivatives of the formula (I), of the present invention are quite novel, and it is not easy to predict from the above compounds already known as $PGI_2$ receptor agonist, that the compounds of the present invention have an activity of $PGI_2$ receptor agonist.

DETAILED DISCLOSURE OF THE INVENTION

The present invention is related to:

1) fused benzeneoxyacetic acid derivatives of the formula (I):

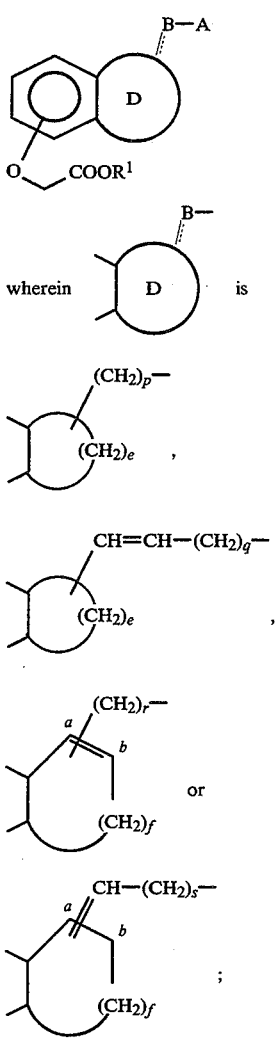

wherein 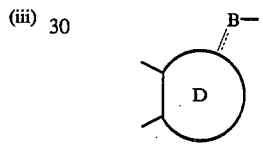 is (i)
$$\begin{array}{c} (CH_2)_p- \\ \diagdown \\ (CH_2)_e \end{array},$$

(ii)
$$\begin{array}{c} CH=CH-(CH_2)_q- \\ \diagdown \\ (CH_2)_e \end{array},$$

(iii)
$$\begin{array}{c} \phantom{a}^a(CH_2)_r- \\ \diagup_b \\ \diagdown \\ (CH_2)_f \end{array} \text{ or}$$

(iv)
$$\begin{array}{c} \phantom{a}^a CH-(CH_2)_s- \\ \diagup_b \\ \diagdown \\ (CH_2)_f \end{array};$$

A is
(i) —COW,
(ii) —NR$^4$—Y or
(iii) —Z—NR$^4$—CONR$^2$R$^3$;
W is
(i) —NR$^2$R$^3$,
(ii) —NR$^4$—OR$^5$,
(iii) —NR$^4$—NR$^2$R$^3$ or
(iv) —NR$^4$—N=CR$^2$R$^3$;
Y is
(i) —CO—R$^5$,
(ii) —CO—U—NR$^2$R$^3$ or
(iii) —CS—U—NR$^2$R$^3$;
Z is
(i) —CH=N— or
(ii) —CH$_2$—NR$^6$—;
R$^1$ is hydrogen atom or C$_{1-4}$ alkyl;
R$^2$ and R$^3$ each, independently, is
(i) hydrogen atom,
(ii) phenyl,
(iii) benzoylphenyl,
(iv) 4–7 membered, unsaturated monocyclic hetero ring containing one nitrogen atom as hetero atom or
(v) C$_{1-4}$ alkyl substituted by 1–3 rings optionally selected from 4–7 membered, unsaturated monocyclic hetero ting containing one nitrogen atom as hetero atom, and phenyl;
R$^4$ is hydrogen atom, C$_{1-6}$ alkyl or phenyl;
R$^5$ is
(i) phenyl,
(ii) 4–7 membered, unsaturated monocyclic hetero ring containing one nitrogen atom as hetero atom or
(iii) C$_{1-4}$ alkyl substituted by 1–3 rings optionally selected from 4–7 membered, unsaturated monocyclic hetero ring containing one nitrogen atom as hetero atom, and phenyl;
R$^6$ is hydrogen atom, C$_{1-6}$ alkyl or phenyl;
U is single bond or C$_{1-4}$ alkylene; the said phenyl and hetero rings may be also substituted by C$_{1-4}$ alkyl, C$_{1-4}$ alkoxy, halogen atom, nitro or trihalomethyl, when R$^2$, R$^3$, R$^4$, R$^5$ or R$^6$ is phenyl or the group containing phenyl, or when R$^2$, R$^3$ or R$^5$ is the said hetero ring or the group containing the hetero ring;
e is 3–5;
f is 1–3;
p is 0–4;
q is 0–2;
r is 0–4;
s is 0–3;
with the proviso that, when A is (ii) —N—R$^4$—Y (in which R$^4$ and Y are the same meaning as hereinbefore defined), q, r, or s is not zero; and that when

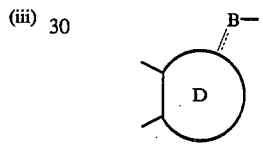

is the formula (iii) or (iv), —(CH$_2$)$_r$ or =CH—(CH$_2$)$_s$ in the side chain should be bonded to the carbon atom at the position a or b in the ring; and non-toxic salts thereof and non-toxic acid addition salts thereof;
2) processes for the preparation thereof and
3) pharmaceutical agents containing them as active ingredient.

Unless otherwise specified, all isomers are included in the present invention. For example, alkyl, alkoxy, alkylene and alkenylene include straight and branched ones. Double bond in alkenylene includes E, Z and EZ mixture. Isomers generated by asymmetric carbon atoms, e.g., branched alkyl are included in the present invention.

The compounds of the formula (I) of the present invention, wherein R$^1$ is hydrogen may be converted into the corresponding salts by methods known per se. Non-toxic and water-soluble salts are preferable. Suitable salts, for example, are salts of alkaline metal (potassium, sodium etc.), salts of alkaline earth metal (calcium, magnesium etc.), ammonium salts, salts of pharmaceutically-acceptable organic amine (tetramethylammonium, triethylamine, methylamine, dimethylamine, cyclopentylamine, benzylamine, phenethylamine, piperidine, monoethanolamine, diethanolamine, tris (hydroxymethyl)amine, lysine, arginine, N-methyl-D-glucamine etc.).

The compounds of the formula (I) may be converted into the corresponding acid additional salts by methods known per se. Non-toxic and water-soluble salts are preferable. Suitable acid addition salts, for example, are salts of inorganic acids, e.g., hydrochloride, hydrobromide, sulphate, phosphate, nitrate etc., or salts of organic acids, e.g., acetate, ladate, tartarate, oxalate, fumarate, maleate, citrate, benzoate, methanesulphonate, ethanesulphonate, benzenesulphonate, toluenesulphonate, isethioate, glucuronate, gluconate etc.

The compounds of the formula (I), salts thereof or acid additional salts thereof may be converted into hydrate thereof by methods known per se.

In the formula (I), $C_{1-4}$ alkyl represented by $R^1$, and $C_{1-4}$ alkyl represented by $R^2$, $R^3$ and $R^5$ mean methyl, ethyl, propyl, butyl and isomers thereof. $C_{1-6}$ alkyl represented by $R^4$ and $R^6$ means methyl, ethyl, propyl, butyl, pentyl, hexyl and isomers thereof.

In the formula (I), 4–7 membered, unsaturated monocyclic hetero ring containing one nitrogen atom as hetero atom, represented by $R^2$, $R^3$ and $R^5$, and existing in the groups represented by $R^2$, $R^3$ and $R^5$ means azepine, pyridine, pyrrole etc.

In the formula (I), $C_{1-4}$ alkylene represented by U mean methylene, ethylene, trimethylene, tetramethylene and isomers thereof.

In the formula (I), $C_{1-4}$ alkyl existing in substituents of the phenyl and hetero ring represented by $R^2$, $R^3$, $R^4$, $R^5$ and $R^6$ means methyl, ethyl, propyl, butyl and isomers thereof, $C_{1-4}$ alkoxy means methoxy, ethoxy, propoxy, butoxy and isomers thereof, halogen means fluorine, chlorine, bromine and iodine atoms, and trihalomethyl means trifluoromethyl, trichloromethyl, tribromomethyl, triiodomethyl.

Examples of representative compounds of the formula (I), of the present invention are listed as follows:

[1-(2-((N,N-Diphenylamino) aminocarbonyl) ethyl) benzocycloheptan-6-yl] oxyacetic acid,

[1-(2E-((N,N-Diphenylamino) aminocarbonyl) vinyl)-indan-4-yl] oxyacetic acid,

[1-(2-((N,N-Diphenylamino) aminocarbonyl)-1E-ethylidene)-indan-4-yl] oxyacetic acid,

[2-(2-((N,N-Diphenylamino) aminocarbonyl) ethyl)-3H-inden-4-yl] oxyacetic acid,

[1-(2-((N,N-Diphenylamino) aminocarbonyl) ethyl)-1,2,3,4-tetrahydronaphthalen-6-yl] oxyacetic acid,

[1-(2-(N-Phenyl-N-(3-pyrrolyl) aminocarbonyl)ethyl)-1,2,3,4-tetrahydronaphthalen-5-yl] oxyacetic acid,

[1-(2-(N-Phenyl-N-(3-azepinyl) aminocarbonyl) ethyl)-1,2,3,4-tetrahydronaphthalen-5-yl] oxyacetic acid,

[1-(2-(N-Phenyl-N-( 1-(3-pyridyl)-1- phenylmethyl) aminocarbonyl)ethyl)-1,2,3,4-tetrahydronaphthalen-5-yl] oxyacetic acid,

[1-(2-(N-Phenyl-N-(diphenylmethyl) aminocarbonyl) ethyl)-1,2,3,4-tetrahydronaphthalen-5-yl] oxyacetic acid,

[1-(2-((1-(3-Pyridyl)-1-phenylmethoxy) aminocarbonyl) ethyl)-1,2,3,4-tetrahydronaphthalen-5-yl] oxyacetic acid,

[1-( 2-(N-Propyl-N-( 1-(3-pyridyl)-1-phenylmethoxy) aminocarbonyl) ethyl)-1,2,3,4-tetrahydronaphthalen-5-yl] oxyacetic acid,

[1-(2-(N-Phenyl-N-(amino) aminocarbonyl) ethyl)-1,2,3,4-tetrahydronaphthalen-5-yl] oxyacetic acid,

[1-(2-((1-(3-Pyridyl)-1-phenylmethylamino )aminocarbonyl)ethyl)-1,2,3,4-tetrahydronaphthalen-5-yl] oxyacetic acid,

[1-(2-(N-Propyl-N-(1-(3-pyridyl)-1-phenylmethylideneamino) aminocarbonyl) ethyl)-1,2,3,4-tetrahydronaphthalen-5-yl] oxyacetic acid,

[1-(2-((2-(3-Pyridyl)-2-phenylethyl) carbonylamino) ethyl)-1,2,3,4-tetrahydronaphthalen-5-yl] oxyacetic acid,

[1-(2-((1-(3-Pyridyl)-1-phenylmethyl) aminocarbonylamino)ethyl)-1,2,3,4-tetrahydronaphthalen-5-yl] oxyacetic acid,

[1-(2-((N-(3-Pyridyl)-N-phenylamino) methylcarbonylamino)ethyl)-1,2,3,4-tetrahydronaphthalen-5-yl]oxyacetic acid,

[1-(2-((1-(3-Pyridyl)-1-phenylmethyl) aminothiocarbonylamino) ethyl)-1,2,3,4-tetrahydronaphthalen-5-yl] oxyacetic acid,

[1-(2-(4-Phenyl-4-(3-pyridyl)-2-phenylsemicarbazono) ethyl)-1,2,3,4-tetrahydronaphthalen-5-yl] oxyacetic acid,

[1-(2-(1-Methyl-4-phenyl-4-(3-pyridyl) semicarbazido) ethyl)-1,2,3,4-tetrahydronaphthalen-5-yl] oxyacetic acid,

[1-(2-(4-( 1-(3-Pyridyl) -1-phenylmethyl)semicarbazido)ethyl)-1,2,3,4-tetrahydronaphthalen-5-yl] oxyacetic acid,

[1-(2-(1-Phenyl-4-(1-(3-pyridyl)-1-phenylmethyl)-semicarbazido) ethyl)-1,2,3,4-tetrahydronaphthalen-5-yl] oxyacetic acid,

[1-(2-((1,1-Di(3-pyridyl)methyl) aminocarbonyl) ethyl)-1,2,3,4-tetrahydronaphthalen-5-yl] oxyacetic acid,

[1-(2E-((1-(3-Azepinyl)-1-phenylmethyl)aminocarbonyl)vinyl-1,2,3,4-tetrahydronaphthalen-5-yl] oxyacetic acid,

[1-(2E-((1-(3-Pyridyl)-1-phenylmethyl)aminocarbonyl)-vinyl-1,2,3,4-tetrahydronaphthalen-5-yl] oxyacetic acid,

[1-(2E-((1-(3-Pyrrolyl)-1-phenylmethyl)aminocarbonyl)vinyl-1,2,3,4-tetrahydronaphthalen-5-yl] oxyacetic acid,

[1-(2E-((1,1-Di(3-pyridyl)methyl)aminocarbonyl)vinyl-1,2,3,4-tetrahydronaphthalen-5-yl]oxyacetic acid,

[1-(2-((1-(3-Azepinyl)-1-phenylmethyl)aminocarbonyl-)ethyl)-3,4- dihydronaphthalen-5-yl] oxyacetic acid,

[1-(2-((1-(3-Pyrrolyl)-1-phenylmethyl)aminocarbonyl-)ethyl)-3,4-dihydronaphthalen-5-yl] oxyacetic acid,

[1-(2-((Diphenylmethyl)aminocarbonyl)ethyl)-3,4-dihydronaphthalen-5-yl] oxyacetic acid,

[1-(2-((1,1-Di(3-pyridyl)methyl)aminocarbonyl)ethyl)-3,4-dihydronaphthalen-5-yl] oxyacetic acid,

[1-(2-((1-(3-Azepinyl)-1-phenylmethyl)aminocarbonyl)-1E-ethylidene)-1,2,3,4-tetrahydronaphthalen-5-yl] oxyacetic acid,

[1-(2-((1-(3-Pyridyl)-1-phenylmethyl)aminocarbonyl)-1-E-ethylidene)-1,2,3,4-tetrahydronaphthalen-5-yl] oxyacetic acid,

[1-(2-((1-(3-Pyrrolyl)-1-phenylmethyl)aminocarbonyl)-1E-ethylidene)-1,2,3,4-tetrahydronaphthalen-5-yl] oxyacetic acid,

[1-(2-((1,1-Di(3-pyridyl)methyl)aminocarbonyl)-1E-ethylidene)- 1,2,3,4-tetrahydronaphthalen-5-yl] oxyacetic acid, and those described in examples below, and further, non-toxic salts thereof and non-toxic acid addition salts thereof.

PROCESSES FOR THE PREPARATION OF THE COMPOUNDS OF THE PRESENT INVENTION

In the compound of the present invention, of the formula (I), (1) compounds of the formula (I), wherein $R^1$ is hydrogen, i.e., the compounds of the formula (IA)

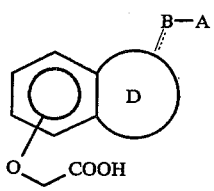 (IA)

wherein all the symbols are the same meaning as hereinbefore defined, may be prepared by the hydrolysis under acidic conditions or alkaline conditions of a compound of the formula (IB):

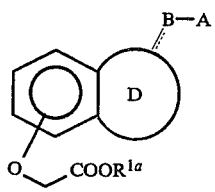 (IB)

wherein $R^{1a}$ is $C_{1-4}$ alkyl and the other symbols are the same meaning as hereinbefore defined.

Such hydrolysis is well known, and for example, the hydrolysis in alkaline conditions may be carried out in an appropriate solvent (e.g., methanol), using a hydroxide or a carbonate of an alkaline metal. The hydrolysis in acidic conditions may be carried out in an aqueous solution of an inorganic acid (e.g., hydrochloric acid) and/or an organic acid (e.g., acetic acid or trifluoroacetic acid etc).

(2) The compounds of the formula (IC):

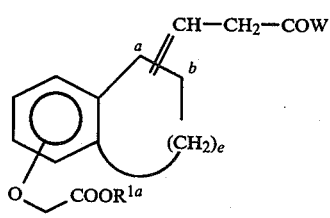 (IC)

wherein all the symbols are the same meaning as hereinbefore defined, may be prepared by reading a compound of the formula (II-11):

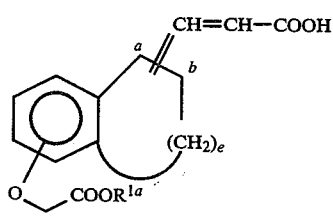 (II-11)

wherein all the symbols are the same meaning as hereinbefore defined, with an amine of the formula (III):

HW  (III)

wherein W is the same meaning as hereinbefore defined, in the presence of an appropriate condensing agent (e.g., 2-chloro-N-methylpyridinum iodide) and a proper base (e.g., triethylamine) at 0° to 40° C.

(3) The compounds of the formula (ID):

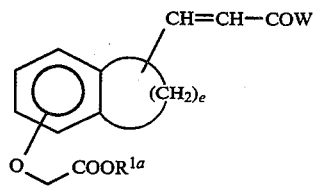 (ID)

wherein all the symbols are the same meaning as hereinbefore defined, may be prepared by subjecting a compound of the formula (II-1):

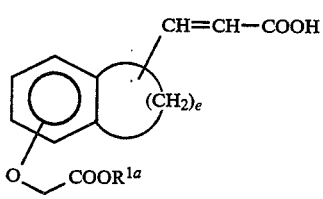 (II-1)

wherein all the symbols are the same meaning as hereinbefore defined, to the reaction for forming an acyl chloride, and then reacting the compound thus obtained, with an amine of the formula (III).

The acyl chloride may be prepared by reacting a carboxylic acid of the formula (II-1) and an acyl halide such as oxalyl chloride, thionyl chloride in an appropriate solvent (e.g., methylene chloride). The reaction of the obtained acyl chloride and an amine of the formula (III) may be carried out in an appropriate solvent (e.g., methylene chloride), in the presence of a base (e.g., triethylamine) at 0° to 40° C.

(4) The compounds of the formula (I), wherein D B is the groups other than ones in the formula (IC) and (ID) and A is COW, i.e., the compounds of the formula (IE):

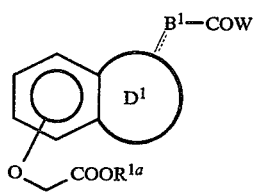 (IE)

wherein

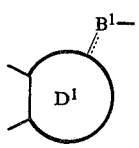

is the same meaning as hereinbefore defined for

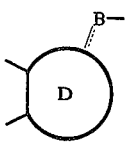

except for

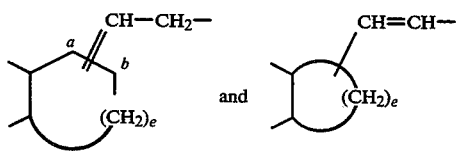

and the other symbols are the same meaning as hereinbefore defined, may be prepared by subjecting a corresponding compound of the formula (II-2):

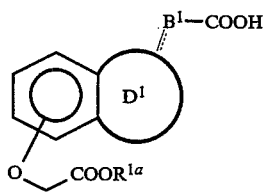

(II-2)

wherein all the symbols are the same meaning as hereinbefore defined, to the amidation with an amine of the formula (III), in the conditions hereinbefore described for step (2) or step (3).

(5) The compounds of the formula (IF):

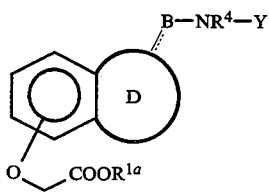

(IF)

wherein all the symbols are the same meaning as hereinbefore defined, may be prepared by reacting a compound of the formula (IV):

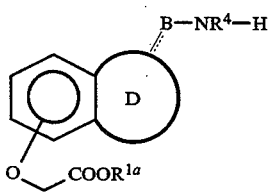

(IV)

wherein all the symbols are the same meaning as hereinbefore defined, with a carboxylic acid or thiocarboxylic acid of the formula (V):

(V)

wherein Y is the same meaning as hereinbefore defined, or with an isocyanate or isothiocyanate, of the formula (VI) or (VII), respectively:

(VI)

or

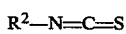

(VII)

wherein $R^2$ is the same meaning as hereinbefore defined.

The amidation reaction of the amine (IV) and the (thio)carboxylic acid (V) may be carried out by the same procedure as hereinbefore described for the step (2) or step (3). The reaction of the amine (IV) and the iso(thio)cyanate [(VI) or (VII)] may be carried out in an appropriate organic solvent (e.g., methylene chloride), in the presence of a base (e.g., triethylamine) at 0° to 40° C.

(6) The compounds of the formula (IG):

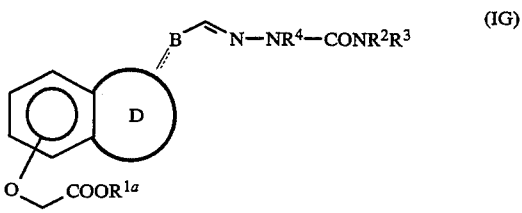

(IG)

wherein all the symbols are the same meaning as hereinbefore defined, may be prepared by reacting a compound of the formula (VIII):

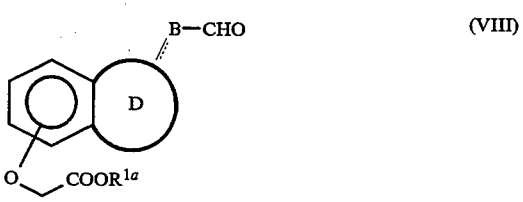

(VIII)

wherein all the symbols are the same meaning as hereinbefore defined, with a semicarbazide of the formula (IX):

(IX)

wherein all the symbols are the same meaning as hereinbefore defined, in an appropriate solvent (e.g., ethanol) at 0° to 40° C. under an atmosphere of inert gas.

(7) The compounds of the formula (IH):

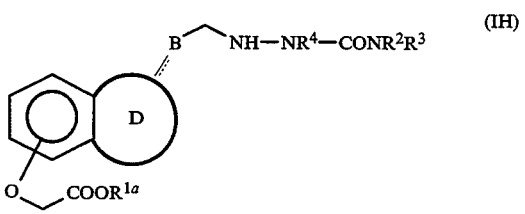

(IH)

wherein all the symbols are the same meaning as hereinbefore defined, may be prepared by the reduction of a compound of the formula (IG) in an alkanol such as methanol, in the presence of an acid (e.g., acetic acid) using a reducing agent such as sodium cyanoborohydride.

(8) The compounds of the formula (IJ)

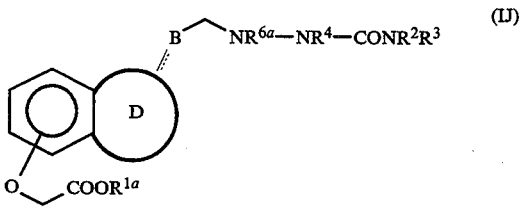

(IJ)

wherein $R^{6a}$ is $C_{1-6}$ alkyl or phenyl and the other symbols are the same meaning as hereinbefore defined, may be prepared by reacting a compound of the formula (IH) with a halide corresponding to $R^{6a}$ ($R^{6a}$ is the same meaning as hereinbefore defined), in an appropriate organic solvent (e.g., methylene chloride) in the presence or absence of an appropriate base (e.g., sodium hydride).

The compounds of the formulae (II-1), (II-2), (IV) and (VIII) used as starting materials in the aforesaid reactions, may be prepared by using a series of reactions depicted in the following Scheme A, B, C and D, wherein DEAD is diethyl azodicarboxylate, Bu is n-butyl,
$^tBu$ is tert-butyl,
Ms is mesyl,
p1 is 0~4,
q1 is 1~2,
r1 is 1~4,
s1 is 1~3, and the other symbols are as the same meaning as hereinbefore defined.

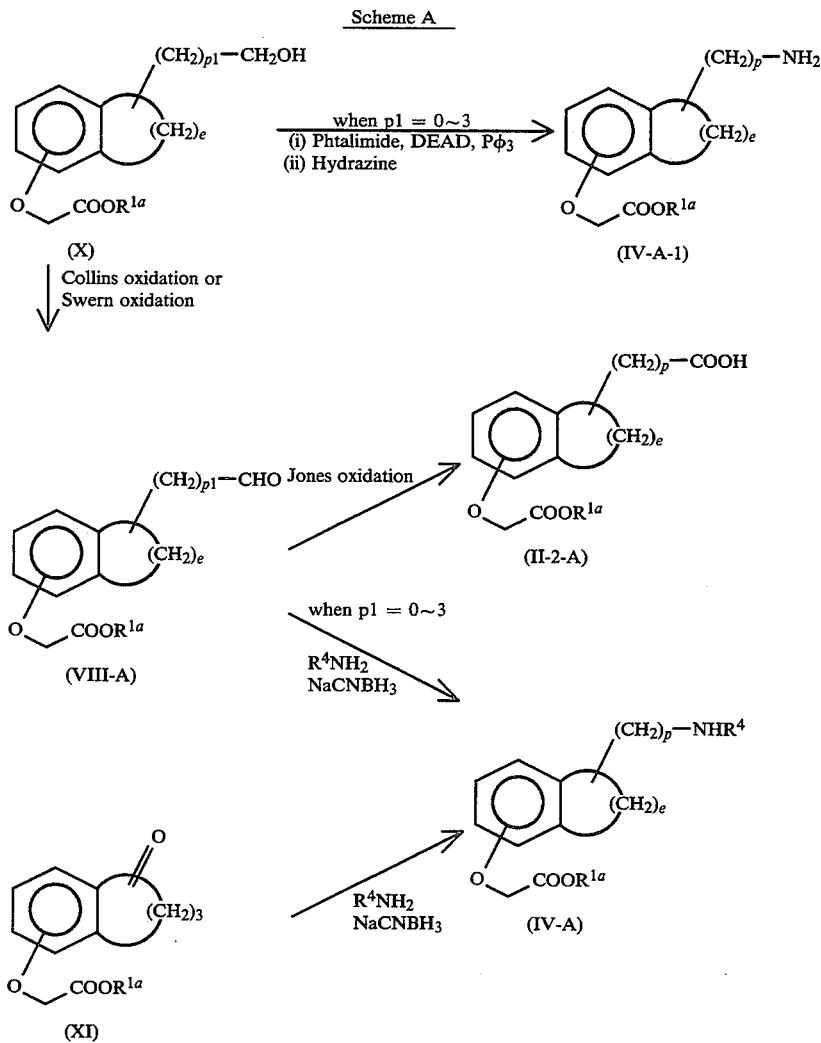

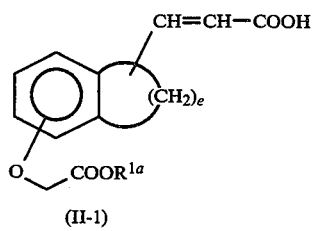

-continued
Scheme B
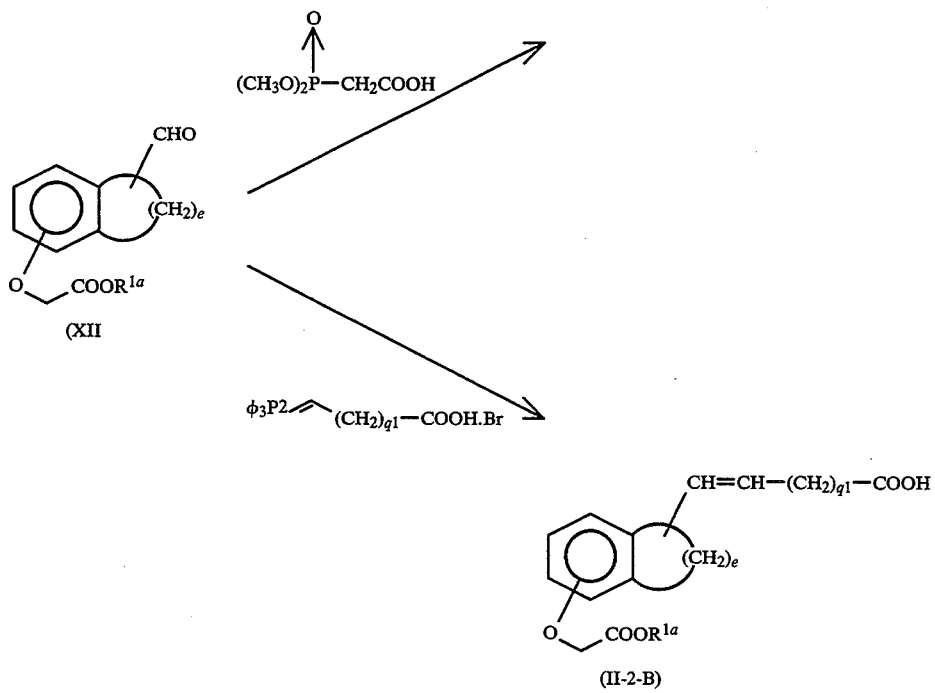
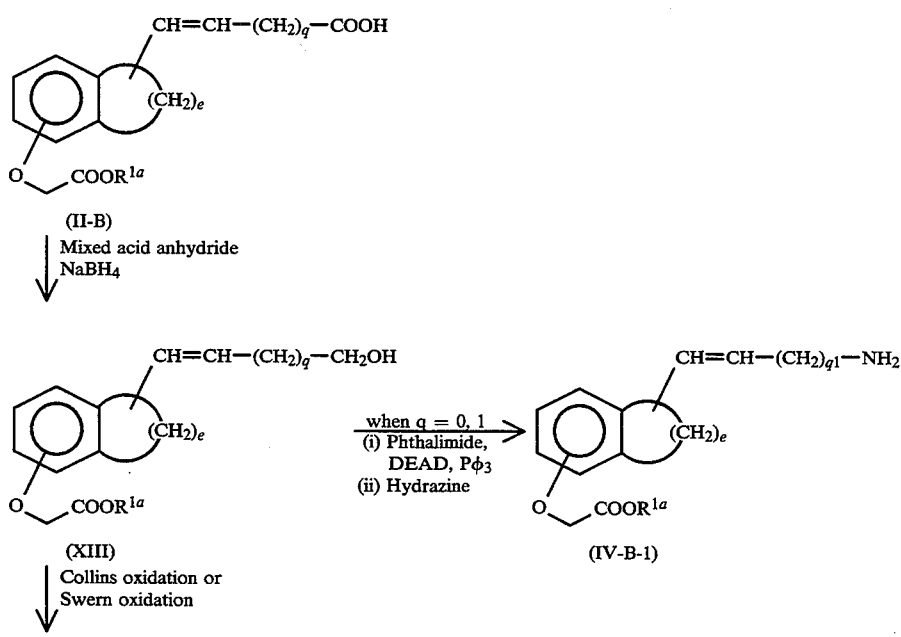
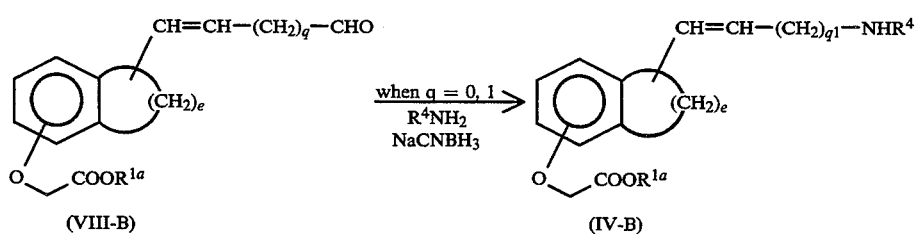

Scheme C
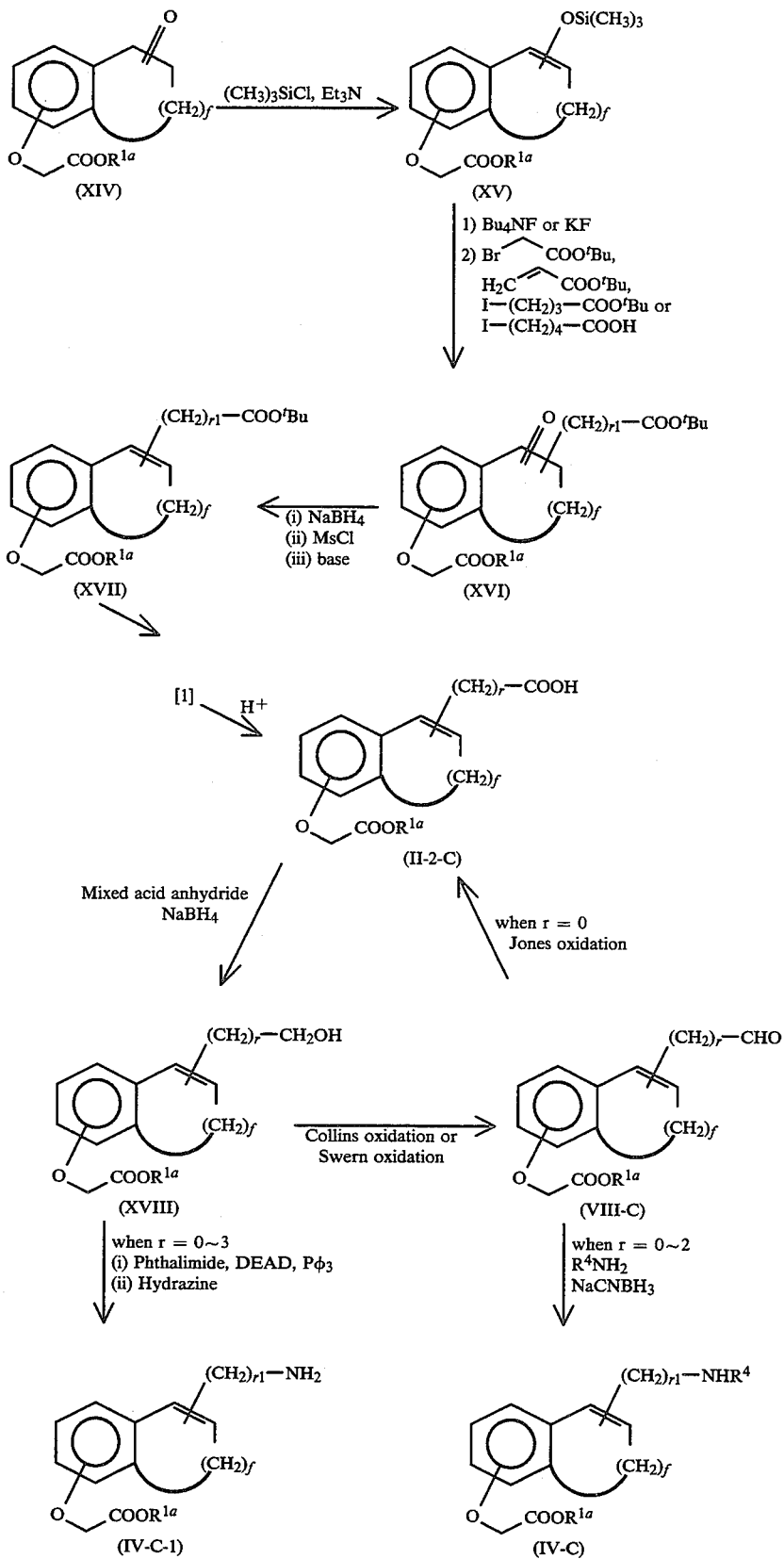

Scheme D

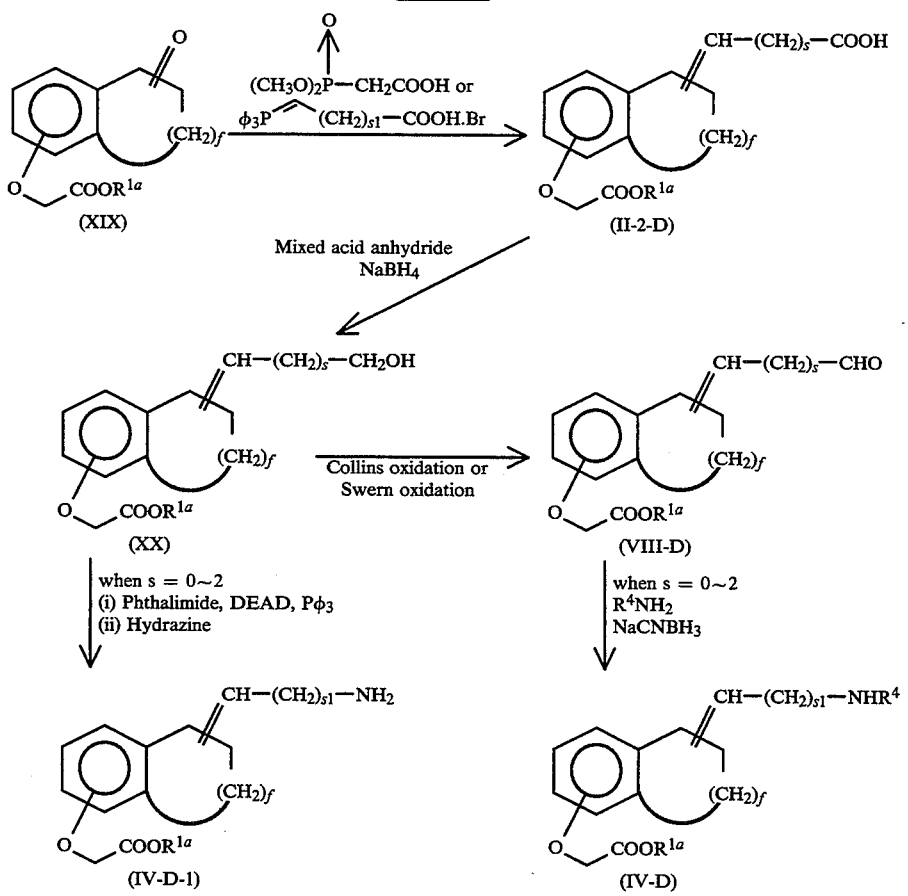

Each of the steps depicted in the said schemes may be carried out by methods known per se.

The compounds of the formula (X), wherein e is 3 or 4 and wherein e is 5, using as starting materials in Scheme A may be prepared by a series of reactions depicted in Scheme E and Scheme F, respectively, wherein DBU is 1,5-diazabicyclo[5,4,0]undec-5-ene,
DIBAL is diisobutylaluminum hydride,
LAH is lithium aluminium hydride,
e1 is 3 or 4,
p2 is 1–4, and the other symbols are as the same meaning as hereinbefore defined.

Scheme [E]-1-(1)

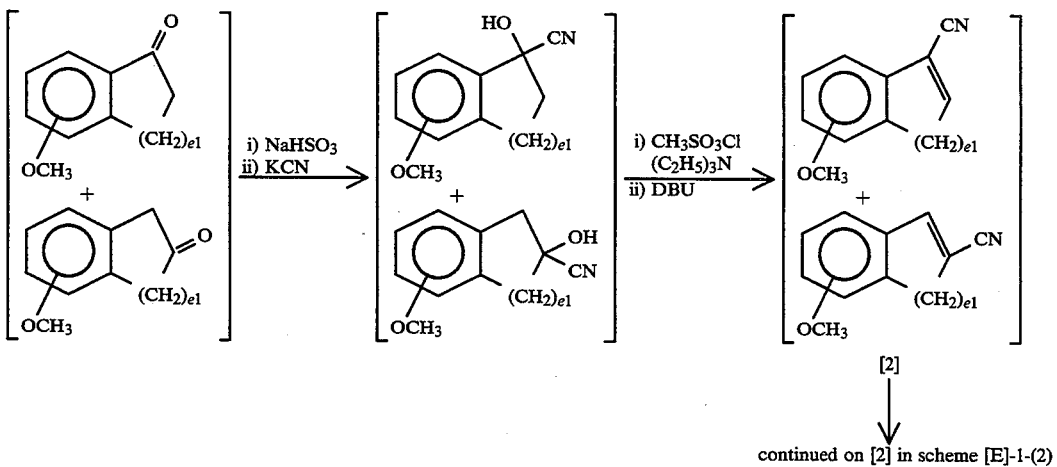

Scheme [E]-1-(2)

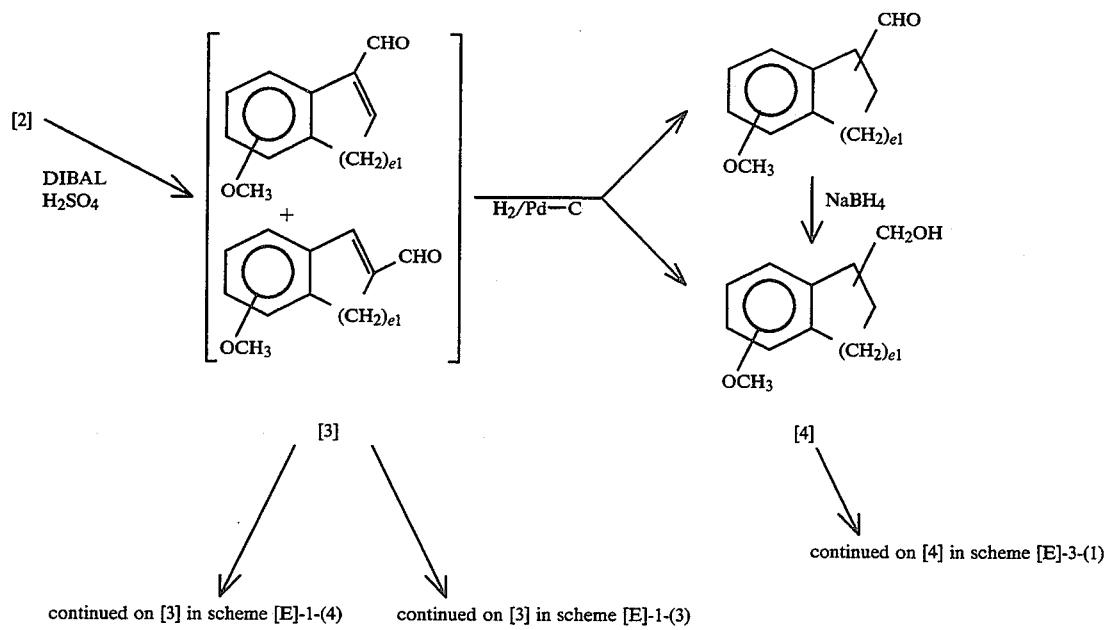
Scheme [E]-1-(3)
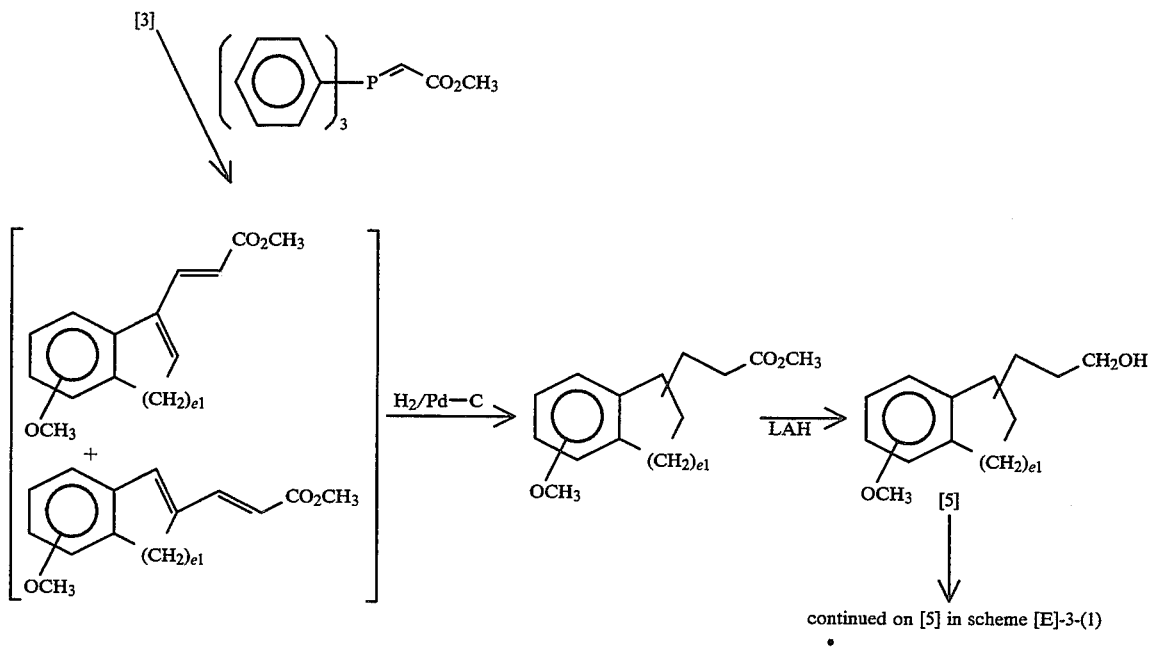
Scheme [E]-1-(4)
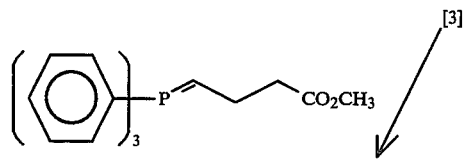

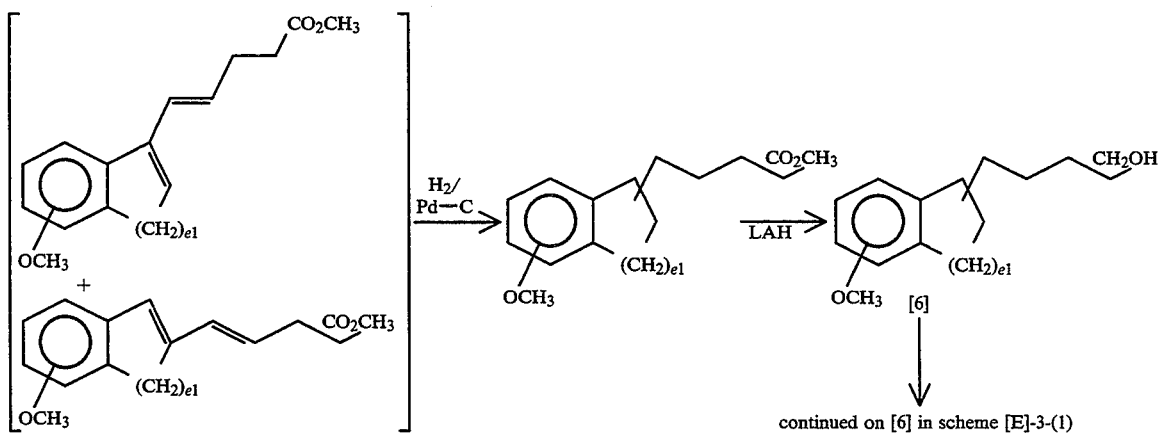
Scheme [E]-2-(1)
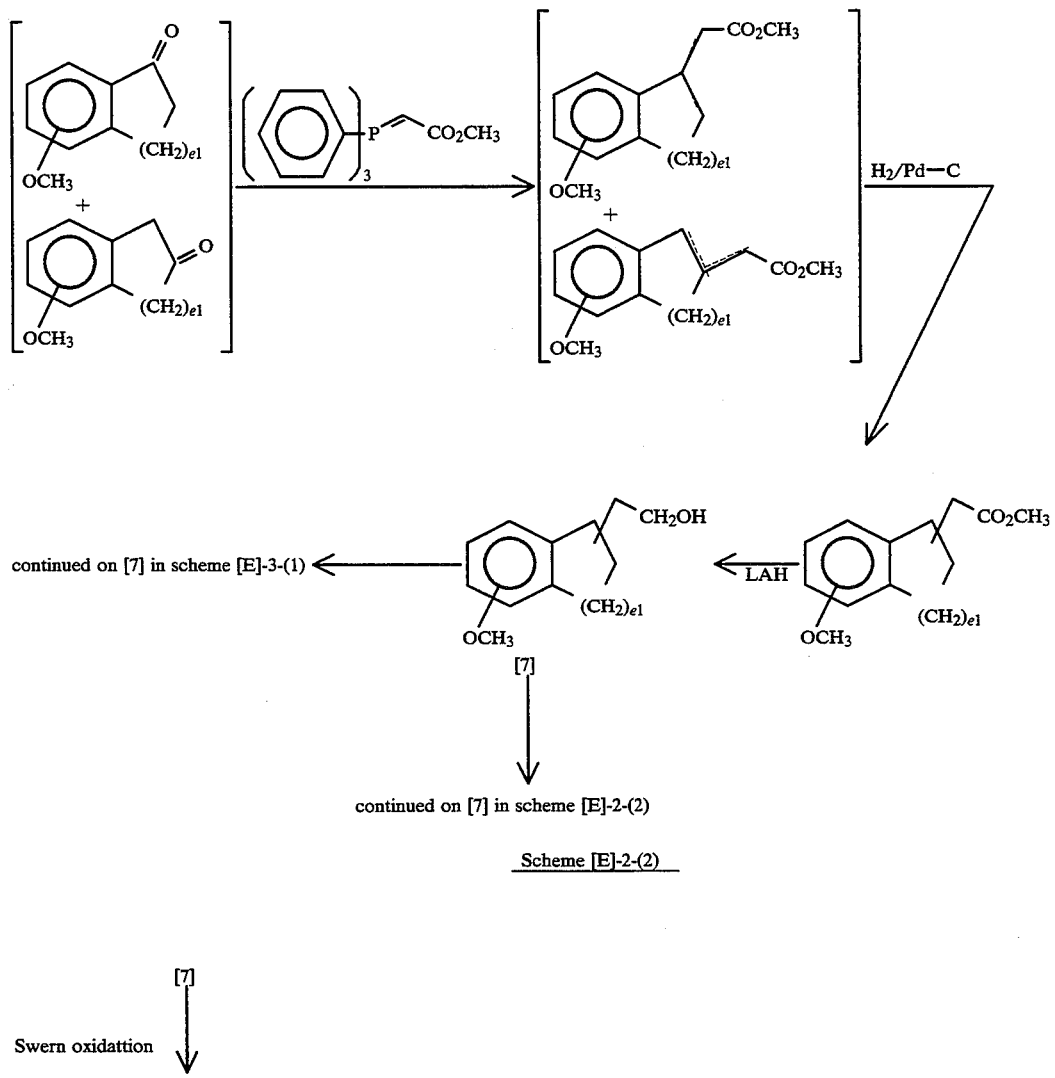
Scheme [E]-2-(2)
[7]
Swern oxidattion ↓

-continued
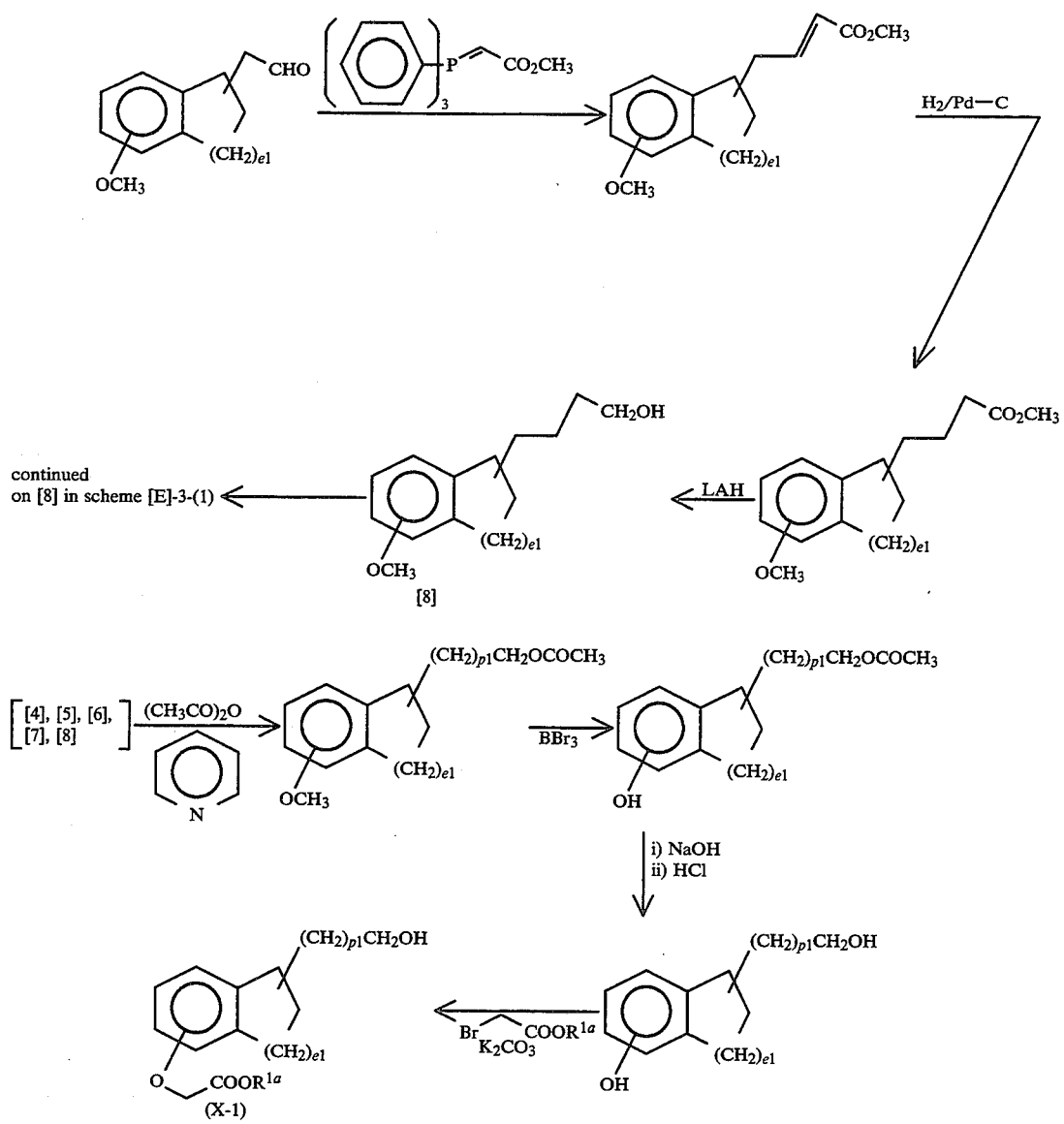
Scheme [F]-1-(1)
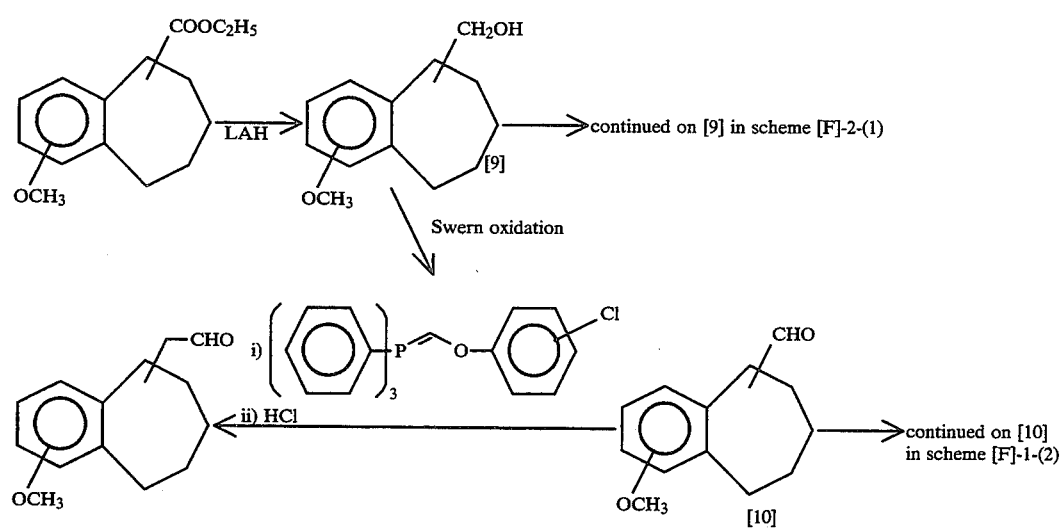

-continued
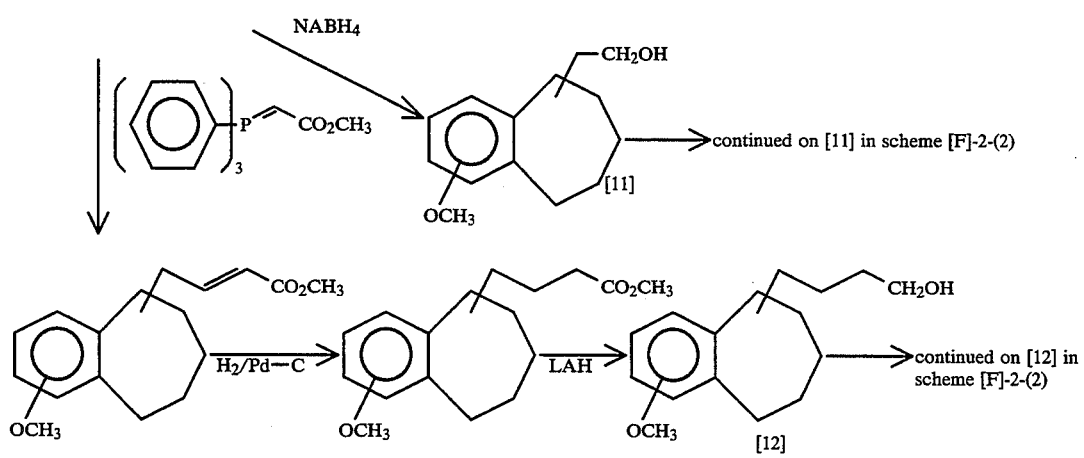
Scheme [F]-1-(2)
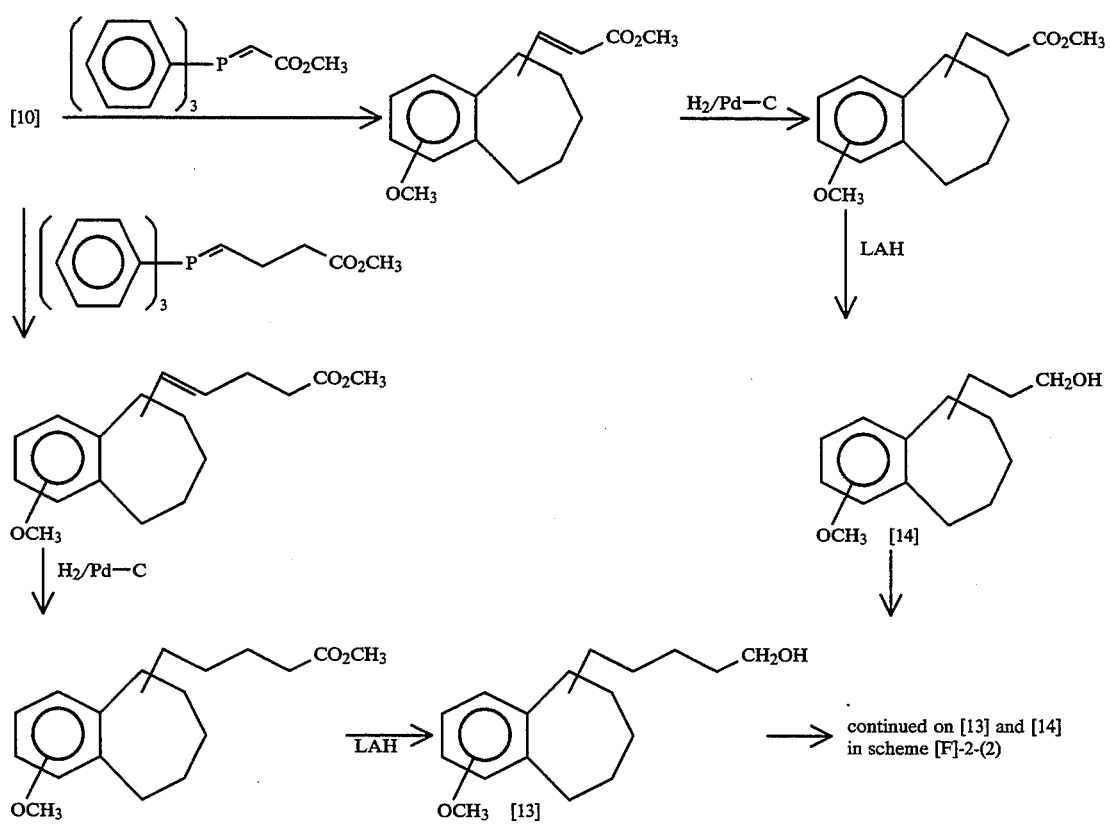
Scheme [F]-2-(1)
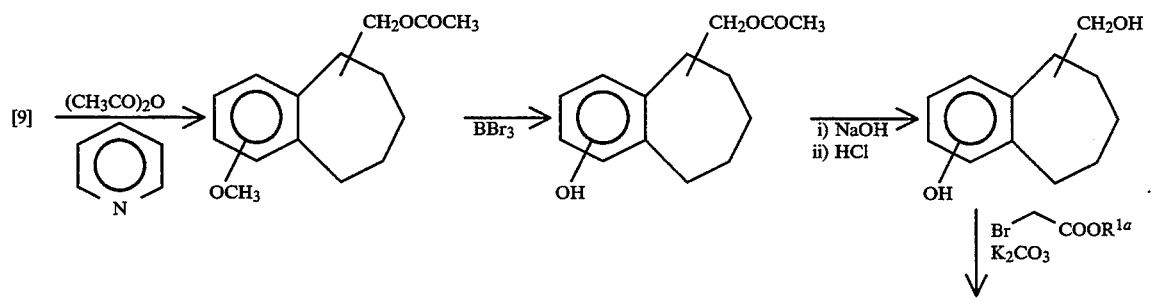

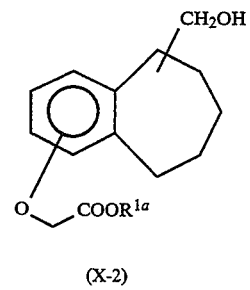

(X-2)

Scheme [F]-2-(2)

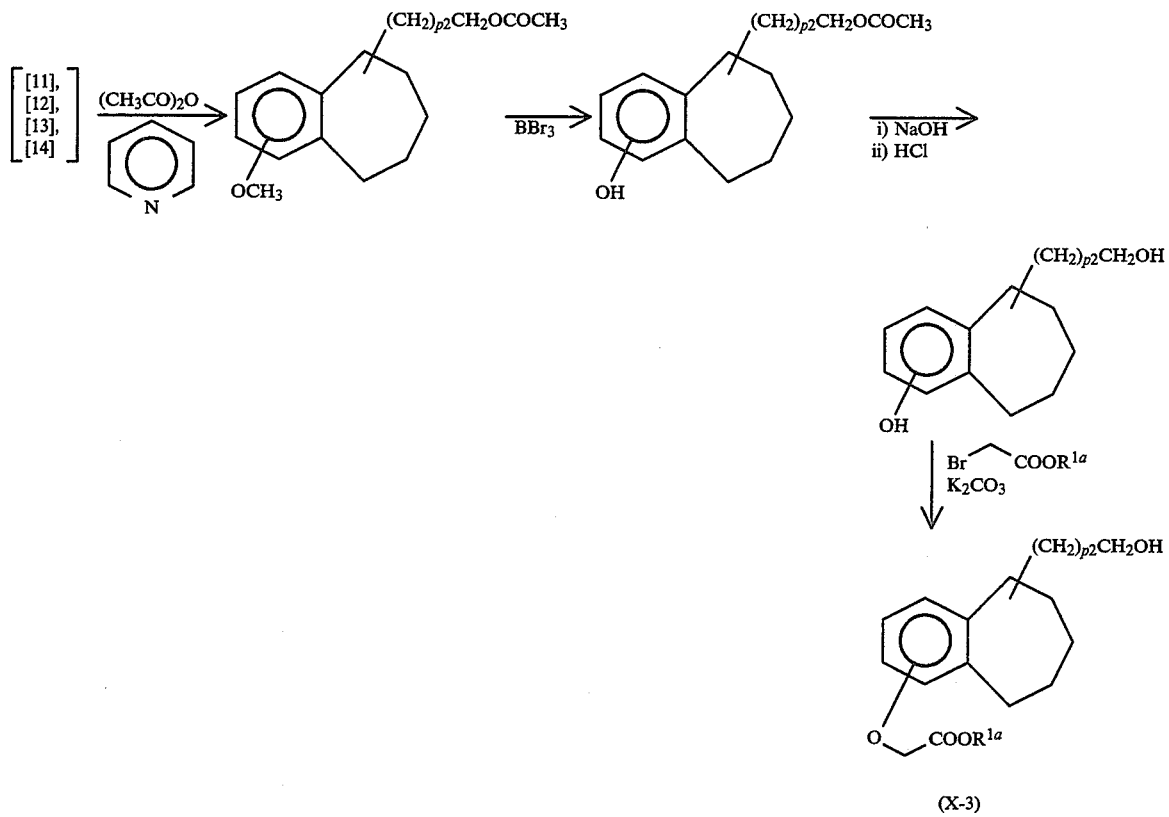

(X-3)

Each of the steps depicted in the said schemes may be carried out by methods known per se.

The compounds of the formulae (XI), (XII), (XIV), (VIII-c) [only a compound wherein r is zero] and (XIX), used as other starting materials are may be easily prepared by methods known pre se, using compounds depicted in Scheme E and F.

Similarly, the compounds of the formulae (III), (V), (VI), (VII) and (IX) are also well known per se, or may be easily prepared by methods known per se.

In each reaction in the present specification, products may be purified by conventional manner. For example, it may be carried out by distillation at atmospheric or reduced pressure, high performance liquid chromatography, thin layer chromatography or column chromatography using silica gel or magnesium silicate, washing or recrystallization. Purification may be carried out after each reaction, or after a series of reactions.

Pharmacological Activities

It has been confirmed that the compounds of the present invention of the formula (I) possess an agonistic activity on $PGI_2$ receptor by the following experimental results.

i) Inhibitory activity on binding of $^3H$-iloprost to $PGI_2$ receptor on human blood platelet membrane fraction Method 50 mM Tris-HCl buffer (pH 7.4) containing 15 mM $MgCl_2$, 5 mM EDTA and 10 nM [$^3H$]-iloprost were used as reaction medium. To 0.2 ml of the reaction medium, human blood platelet membrane fraction (0.3 mg protein) was added with or without a test compound. The mixture was incubated at 24° C. for 30 min. After incubation, 4 ml of ice-cold 10 mM Tris-HCl buffer (pH 7.4) was added to the reaction mixture, and filtered through Whatman GF/B glass fiber filter, and washed 4 times with 4 ml of ice-cold 10 mM Tris-HCl buffer (pH 7.4) to separate bound and free [$^3H$]-iloprost. After washing, the filter was dried and radioactivity was counted. Non-specific binding was obtained by performing parallel binding experiments in the presence of 10 μM non-labelled iloprost. Specific binding was calculated by subtracting the non-specific binding from the total binding.

The inhibitory effect of test compound was calculated from the following equation.

*The percentage of inhibition* (%) = $100 - (B_1/B_0 \times 100)$ $B_1$: specific [$^3$H]-iloprost binding in presence of test compound $B_0$: specific [$^3$H]-iloprost binding in absence of test compound The results are shown in the following table 1.

TABLE 1

| Ex. No. | IC$_{50}$ (μM) |
|---|---|
| 3 | 0.68 |
| 3 (j) | 7.6 |
| 3 (l) | 2.9 |
| 3 (m) | 0.32 |
| 3 (o) | 0.21 |
| 3 (p) | 0.0094 |
| 3 (q) | 6.8 |
| 3 (v) | 0.12 |
| 3 (w) | 0.02 |
| 3 (x) | 2.7 |
| 3 (y) | 1.8 |
| 3 (z) | 0.1 |
| 3 (aa) | 6.0 |
| 3 (bb) | 4.1 |
| 3 (cc) | 2.7 |
| 3 (dd) | 1.7 |
| 4 (a) | 2.3 |
| 7 | 6.6 |
| 8 (b) | 3.1 |
| 8 (c) | 0.18 |
| 8 (d) | 1.8 |
| 10 (a) | 0.48 |
| 10 (b) | 8.4 |
| 10 (c) | 1.3 | ii) Inhibitory effect on human blood platelet aggregation

Method

Platelet-rich plasma (PRP) was prepared from human blood ($5 \times 10^5$ platelets/mm$^3$), and a test compound was added to PRP 1 min prior to the addition of ADP (4 μm). the aggregation as monitored using a platelet aggregometer (NBS HEMA TRACER 601, Niko Bioscience, Japan). The results are shown in the following table 2.

TABLE 2

| Ex. No. | IC$_{50}$ (μM) |
|---|---|
| 3 (l) | 8.3 |
| 3 (m) | 2.8 |
| 3 (o) | 0.40 |
| 3 (p) | 0.11 |
| 3 (v) | 1.0 |
| 3 (w) | 0.62 |
| 3 (y) | 7.0 |
| 3 (z) | 2.3 |
| 3 (dd) | 5.1 |
| 8 (b) | 8.0 |
| 8 (c) | 2.5 |
| 8 (d) | 5.6 |

Toxicity

The toxicity of the compounds of the present invention, of the formula (I) is very low and therefore, it may be confirmed that the compounds of the present invention are fully safe for pharmaceutical use.

Application for Pharmaceuticals

The compounds of the present invention, of the formula (I) possess an agonistic activity on PGI$_2$ receptor, and therefore are useful for the prevention and/or the treatment of thrombosis, arteriosclerosis, ischemic heart diseases, gastric ulcer and hypertension, etc.

For the purpose above described, the compounds of the formula (I), of the present invention, non-toxic salts thereof, acid additional salts thereof and hydrates thereof may be normally administered systemically or partially, usually by oral or parenteral administration.

The doses to be administered are determined depending upon age, body weight, symptom, the desired therapeutic effect, the route of administration, and the duration of the treatment etc. In the human adult, the doses per person per dose are generally between 1 mg and 1000 mg, by oral administration, up to several times per day, and between 100 μg and 100 mg, by parenteral administration up to several times per day, or continuous administration between 1 and 24 hrs. per day from vein.

As mentioned above, the doses to be used depend upon various conditions. Therefore, there are cases in which doses lower than or greater than the ranges specified above may be used.

When administration of the compounds of the present invention, it is used as solid compositions, liquid compositions or other compositions for oral administration, as injections, liniments or suppositories etc. for parenteral administration.

Solid compositions for oral administration include compressed tablets, pills, capsules, dispersible powders, and granules. Capsules include hard capsules and soft capsules.

In such compositions, one or more of the active compound(s) is or are admixed with at least one inert diluent (such as lactose, mannitol, glucose, hydroxypropyl cellulose, microcrystalline cellulose, starch, polyvinylpyrrolidone, magnesium metasilicate aluminate, etc.). The compositions may also comprise, as is normal practice, additional substances other than inert diluents: e.g. lubricating agents (such as magnesium stearate etc.), disintegrating agents (such as cellulose calcium glycolate, etc.), stabilizing agents (such as lactose, etc.), and assisting agents for dissolving (such as glutamic acid, asparaginic acid etc.).

The tablets or pills may, if desired, be coated with a film of gastric or enteric material (such as sugar, gelatin, hydroxypropyl cellulose or hydroxypropylmethyl cellulose phthalate etc.), or be coated with more than two films. And further, coating may include containment within capsules of absorbable materials such as gelatin.

Liquid compositions for oral administration include pharmaceutically-acceptable solutions, emulsions, suspensions, syrups and elixirs. In such compositions, one or more of the active compound(s) is or are contained in inert diluent(s) commonly used in the art (purified water, ethanol etc.). Besides inert diluents, such compositions may also comprise adjuvants (such as wetting agents, suspending agents, etc.), sweetening agents, flavouring agents, perfuming agents, and preserving agents.

Other compositions for oral administration include spray compositions which may be prepared by known methods and which comprise one or more of the active compound(s). Spray compositions may comprise additional substances other than inert diluents: e.g. stabilizing agents (sodium sulfate etc.), isotonic buffer (sodium chloride, sodium citrate, citric acid, etc.). For preparation of such spray compositions, for example, the method described in the U.S. Pat. No. 2868691 or 3095355 (herein incorporated in their entireties by reference) may be used.

Injections for parenteral administration include sterile aqueous or non-aqueous solutions, suspensions and emulsions. In such compositions, one more of active compound(s) is or are admixed with at least one of inert aqueous diluent(s) (distilled water for injection, physiological salt solution etc.) or inert non-aqueous diluent(s) (propylene glycol, polyethylene glycol, olive oil, ethanol, POLYSOLBATE80 (registered trade mark)etc.).

Injections may comprise additional other than inert diluents: e.g. preserving agents, wetting agents, emulsifying agents, dispersing agents, stabilizing agent (lactose etc.), assisting agents such as assisting agents for dissolving (glutamic acid, asparaginic acid etc.).

They may be sterilized for example, by filtration through a bacteria-retaining filter, by incorporation of sterilizing agents in the compositions or by irradiation. They may also be manufactured in the form of sterile solid compositions, for example, by freeze-drying, and which may be dissolved in sterile water or some other sterile diluent(s) for injection immediately before used.

Other compositions for parenteral administration include liquids for external use, and endermic liniments, ointment, suppositories and pessaries which comprise one or more of the active compound(s) and may be prepared by per se known methods.

REFERENCE EXAMPLE AND EXAMPLES

The following reference examples and examples are intended to illustrate, but not limit, the present invention.

The solvents in parentheses show the developing or eluting solvents and the ratios of the solvents used are by volume in chromatographic separations.

Unless otherwise specified, "IR" was measured by KBr method, "NMR" was measured in a solution of CDCl$_3$, and "mp." means melting point.

REFERENCE EXAMPLE 1

Methyl (1-formyl-1,2,3,4-tetrahydronaphthalen-5-yl) oxyacetate

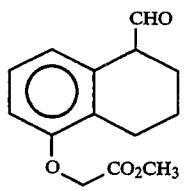

A mixture of chromium(VI) oxide (14.5 g) and pyridine (23.7 ml) in methylene chloride (460 ml) was stirred at 25° C. for 30 min under an atmosphere of argon. To the mixture were added successively dry Celite (registered trade mark) and a solution of methyl (1-hydroxymethyl-1,2,3,4-tetrahydronaphthalen-5-yl) oxyacetate (1.10 g)in methylene chloride (100 ml). After stirred for 15 min, the mixture was vigorously stirred by addition of sodium bisulfate monohydrate. The mixture was diluted with ether, filtered, and concentrated to give the title compound (1.08 g) having the following physical data. The obtained compound was used without purification in the next reaction.

TLC: Rf 0.40 (ethyl acetate:hexane=3:7);

IR (cm$^{-1}$): $\nu$ 2937, 1761, 1722, 1584, 1465, 1438, 1378, 1346, 1280, 1210, 1120, 1027, 779.

REFERENCE EXAMPLE 2

Methyl (1-carboxyl-1,2,3,4-tetrahydronaphthalen-5-yl) oxyacetate

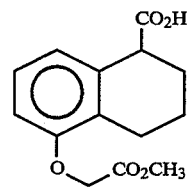

A solution of the aldehyde prepared in reference example 1 (1.08 g) in acetone (80 ml) was cooled at 0° C. After to the solution was added Jones reagent (1.0 ml), the mixture was stirred for 20 min at 0° C. To the mixture was added isopropyl alcohol (1 ml). After stirred for 10 min, water and ether were added thereto, and the mixture was extracted with ether. The extract was washed with water, dried over anhydrous magnesium sulfate and evaporated. The residue was recrystallized from ethyl acetate-hexane to give the title compound (790 mg) having the following physical data.

TLC: Rf 0.20 (ethyl acetate:hexane=2:3);

mp.: 104°~105° C.

REFERENCE EXAMPLE 3

Methyl (2-aminomethyl-1,2,3,4-tetrahydronaphthalen-5-yl) oxyacetate

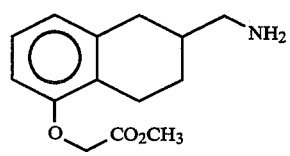

To a solution of methyl (2-hydroxymethyl-1,2,3,4-tetrahydronaphthalen-5-yl) oxyacetate (1.15 g), phthalimide (1.22 g) and triphenylphosphine (2.17 g) in tetrahydrofuran (50 ml) was added diethyl azodicarboxylate (1.6 ml) at 20° C. After stirred for 2 h, the mixture was quenched by addition of water. The mixture was extracted with ether. The extract was washed with a saturated aqueous solution of sodium chloride, dried over anhydrous magnesium sulfate and evaporated. To a solution of the obtained residue in ethanol (30 ml) was added hydrazine monohydrate (0.7 ml) at room temperature. The mixture was stirred overnight. The mixture was quenched by addition of water (20 ml) and evaporated. The residue was crystallized from 2N hydrochloric acid (20 ml) to give the title compound (700 mg) having the following physical data.

TLC: Rf 0.22 (methanol:methylene chloride=1:9).

REFERENCE EXAMPLE 4

Methyl (2-methylaminomethyl-1,2,3,4-tetrahydronaphthalen-5-yl) oxyacetate

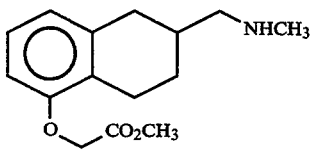

To a solution of methyl (2-formyl-1,2,3,4-tetrahydronaphthalen-5-yl) oxyacetate (0.93 g) obtained by the same procedure as reference example 1, and methylamine (0.58 g, in 40% methanol)in methanol (47 ml) was added sodium cyanoborohydride at 0° C. After to the solution was added dropwise acetic acid until pH 4, the mixture was stirred for 15 h at room temperature. The mixture was concentrated under reduce pressure until the volume of the solution became about 10 ml. After the addition of 1N hydrochloric acid until pH 1, ice water and methylene chloride were added thereto and the mixture was mildly alkalified by adding sodium bicarbonate. The mixture was extracted with methylene chloride. Separated organic layer was washed with a saturated aqueous solution of sodium chloride, dried over anhydrous magnesium sulfate, and evaporated. The residue was washed with ethyl acetate-hexane to give the title compound (0.419 g) having the following physical data.

NMR: δ7.03(1H, t, J=7.5Hz), 6.76(1H, d, J=7.5 Hz), 6.50(1H, d, J=7.5 Hz), 4.63(2H, s), 3.80(3H, s), 3.2~2.8(4H, m), 2.73(3H, s), 2.8~2.5(2H, m), 2.5~1.4(4H, m).

EXAMPLE 1

Methyl (1-dibenzylaminocarbonyl-1,2,3,4-tetrahydronaphthalen-5-yl) oxyacetate

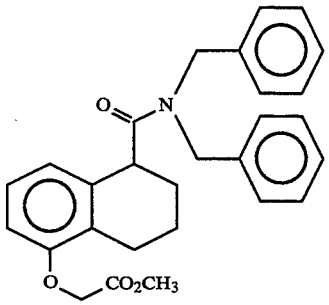

A solution of the compound prepared in reference example 2 (150 mg), 2-chloro-N-methylpyridinum iodide (218 mg), dibenzylamine (145 mg) and triethylamine (0.239 ml)in methylene chloride (6 ml) was stirred overnight at room temperature. The mixture was poured into 1N hydrochloric acid. The mixture was extracted with ether. The extract was washed with water and a saturated aqueous solution of sodium chloride, successively, dried over anhydrous magnesium sulfate, and evaporated. The residue was purified by silica gel column chromatography (hexane:ethyl acetate=3:2) to give the title compound (207 mg) having the following physical data.

NMR: δ7.50~7.20 (10H, m), 7.03 (1 H, t, J=8 Hz), 6.61 (1H, d, J=8 Hz), 6.55 (1 H, d, J=8 Hz), 4.69 (2H, s), 4.61 (2H, s), 4.57(2H, s), 4.10 (1H, m), 3.77 (3H, s), 2.79 (2H, m), 2.20~1.90 (3H, m), 1.65 m).

EXAMPLE 2

(1-Dibenzylaminocarbonyl-1,2,3,4-tetrahydronaphthalen-5-yl) oxyacetic acid

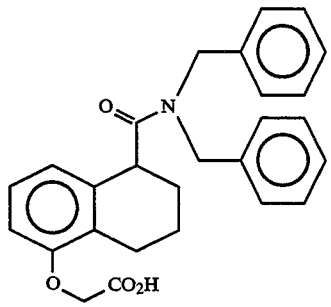

To a solution of the compound prepared in example 1 (204 mg) in dimethoxyethane (3 ml) and methanol (2 ml) was added 1N aqueous solution of sodium hydroxide. After stirred for 2 h, the mixture was quenched by addition of 1N hydrochloric acid. The mixture was extracted with ethyl acetate. The extract was washed with water and a saturated aqueous solution of sodium chloride, dried over anhydrous magnesium salfate, and evaporated. The residue was purified by silica gel column chromatography (ethyl acetate:hexane=1:-4→ethyl acetate) to give the title compound (171 mg) having the following physical data.

TLC: Rf 0.13 (methanol:methylene chloride=1:9);
IR(cm⁻¹): ν 3031, 2936, 1737, 1584, 1496, 1464, 1435, 1361, 1208, 1117, 1076, 1029, 886, 735, 700.

EXAMPLE 2(a)~2(h)

By the same procedure as example 2, the compounds shown in the following table 3 were given by using various esters obtained from the compound prepared in reference example 2 by the same procedure as example 1 (proviso that corresponding proper amines were used instead of dibenzylamine).

TABLE 3

| Ex. No. | Structure | TLC | IR (cm⁻¹) |
|---|---|---|---|
| 2 (a) | 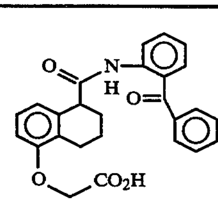 | Rf = 0.13 (CH₃OH:CH₂Cl₂ = 1:9) | ν 3300, 2936, 1737, 1640, 1581, 1515, 1446, 1261, 1116, 1073, 943, 753, 701, 641. |

TABLE 3-continued

| Ex. No. | Structure | TLC | IR (cm$^{-1}$) |
|---|---|---|---|
| 2 (b) | 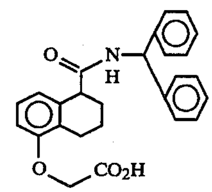 | Rf = 0.13 (CH$_3$OH:CH$_2$Cl$_2$ = 1:9) | ν 3272, 2927, 1740, 1646, 1583, 1528, 1494, 1463, 1430, 1253, 1226, 1122, 729, 698. |
| 2 (c) | 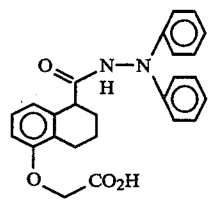 | Rf = 0.09 (CH$_3$OH:CH$_2$Cl$_2$ = 1:9) | ν 3262, 2932, 1737, 1700, 1669, 1589, 1519, 1494, 1464, 1314, 1275, 1231, 1176, 1123, 1072, 941, 747, 691, 625. |
| 2 (d) | 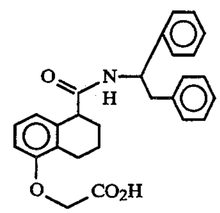 | Rf = 0.09 (CH$_3$OH:CH$_2$Cl$_2$ = 1:9) | ν 3318, 3030, 2936, 1748, 1645, 1585, 1531, 1496, 1464, 1431, 1318, 1248, 1126, 909, 757, 700, 540. |
| 2 (e) | 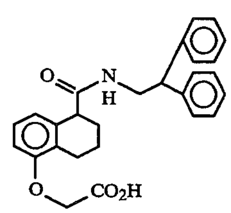 | Rf = 0.13 (CH$_3$OH:CH$_2$Cl$_2$ = 1:9) | ν 3396, 2951, 1733, 1625, 1584, 1531, 1460, 1356, 1282, 1223, 1123, 890, 786, 767, 754, 739, 703, 627, 539, 493. |
| 2 (f) | 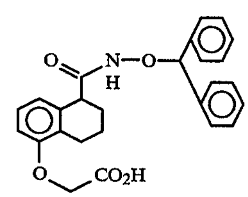 | Rf = 0.09 (CH$_3$OH:CH$_2$Cl$_2$ = 1:9) | ν 3278, 2932, 1733, 1637, 1585, 1495, 1462, 1364, 1283, 1224, 1123, 1080, 1037, 892, 762, 704, 559, 494, 449. |
| 2 (g) | 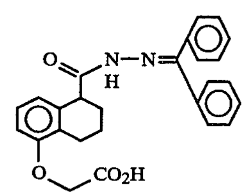 | Rf = 0.13 (CH$_3$OH:CH$_2$Cl$_2$ = 1:9) | ν 3303, 2934, 1746, 1641, 1584, 1510, 1491, 1464, 1445, 1328, 1273, 1202, 1112, 1074, 895, 777, 703, 651, 591. |
| 2 (h) | 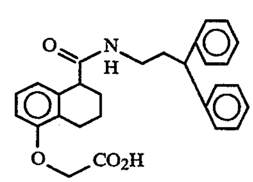 | Rf = 0.13 (CH$_3$OH:CH$_2$Cl$_2$ = 1:9) | ν 3348, 2933, 1741, 1647, 1582, 1527, 1495, 1466, 1427, 1315, 1252, 1126, 922, 747, 698. |

The compounds shown in the table 3 are named as follows:

2(a) [1-(2-Benzoylphenylaminocarbonyl)-1,2,3,4-tetrahydronaphthalen-5-yl] oxyacetic acid 2(b) [1-(Diphenylmethylaminocarbonyl)-1,2,3,4-tetrahydronaphthalen-5-yl] oxyacetic acid 2(c) [1-((N, N-Diphenylamino) aminocarbonyl)-1,2,3,4-tetrahydronaphthalen-5-yl] oxyacetic acid 2(d) [1-((1,2-Diphenylethyl)aminocarbonyl)-1,2,3,4-tetrahydronaphthalen-5-yl] oxyacetic acid 2(e) [1-((2,2-Diphenylethyl)aminocarbonyl)-1,2,3,4-tetrahydronaphthalen-5-yl] oxyacetic acid 2(f) [1-(Diphenylmethoxyaminocarbonyl)-1,2,3,4-tetrahydronaphthalen-5-yl] oxyacetic acid 2(g) [1-((Diphenylmethylideneamino)aminocarbonyl)-1,2,3,4-tetrahydronaphthalen-5-yl] oxyacetic acid 2(h) [1-((3,3-Diphenylpropyl)aminocarbonyl)-1,2,3,4-tetrahydronaphthalen-5-yl] oxyacetic acid

EXAMPLE 3

[1-(2-Diphenylaminocarbonylethyl)-1,2,3,4-tetrahydronaphthalen-5-yl] oxyacetic acid

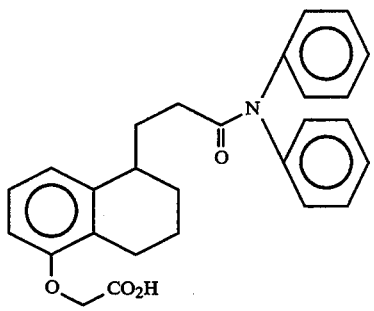

By the same procedure as reference example 1→reference example 2→example 1 (using diphenylamine instead of dibenzylamine), using methyl [1-(3-hydroxypropyl)-1,2,3,4-tetrahydronaphthalen-5-yl] oxyacetate instead of methyl (1-hydroxymethyl-1,2,3,4-tetrahydronaphthalen-5-yl) oxyacetate, was obtained methy [1-(2-diphenylaminocarbonylethyl)-1,2,3,4-tetrahydro naphthalen-5-yl] oxyacetate. By the same procedure as example 2, using methyl [1-( 2-diphenylaminocarbonylethyl)-1,2,3,4-tetrahydronaphtahalen-5-yl] oxyacetate thus obtained, the title compound having the following physical data was given.

TLC: Rf 0.15 (methanol:methylene chloride=1:9);

IR(cm$^{-1}$): $\nu$ 2932, 1737, 1671, 1626, 1583, 1493, 1462, 1389, 1274, 1235, 1117, 1076, 1005, 882, 758, 703, 591.

EXAMPLE 3(a)~3(ss)

By the same procedure as example 3, the compounds shown in the following table 4 were given by using corresponding acetate instead of methyl [2-(3-hydroxypropyl)-1,2,3,4-tetrahydronaphthalen-5-yl] oxyacetate, and corresponding amine.

TABLE 4

| Ex. No. | Structure | TLC | IR (cm$^{-1}$) |
|---|---|---|---|
| 3(a) | 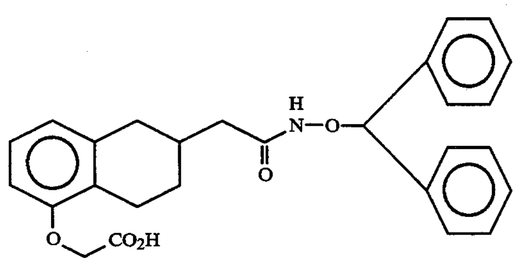 | Rf = 0.17 (CH$_3$OH:CHCl$_3$ = 3:15) | $\nu$ 3253, 3031, 2926, 1723, 1635, 1585, 1465, 1227, 1210, 1124, 1037, 763, 712, 706. |
| 3(b) | 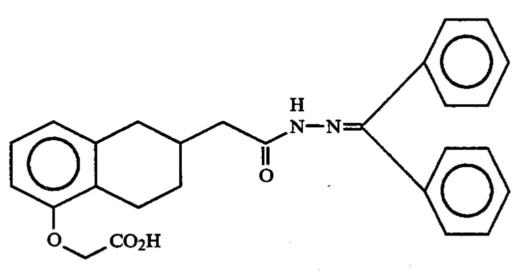 | Rf = 0.25 (CH$_3$OH:CHCl$_3$ = 3:15) | $\nu$ 3140, 2936, 1743, 1643, 1587, 1466, 1368, 1275, 1248, 1219, 1123, 774, 693. |
| 3(c) | 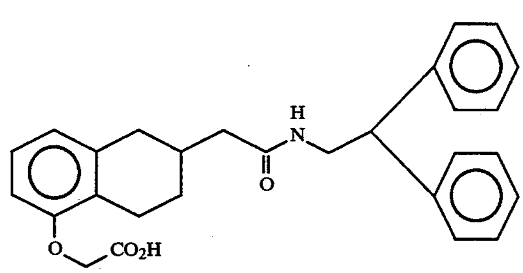 | Rf = 0.25 (CH$_3$OH:CHCl$_3$ = 3:15) | $\nu$ 3343, 2925, 1747, 1645, 1544, 1467, 1431, 1253, 1124, 928, 764, 735, 697. |

TABLE 4-continued

| Ex. No. | Structure | TLC | IR (cm$^{-1}$) |
|---|---|---|---|
| 3(d) | 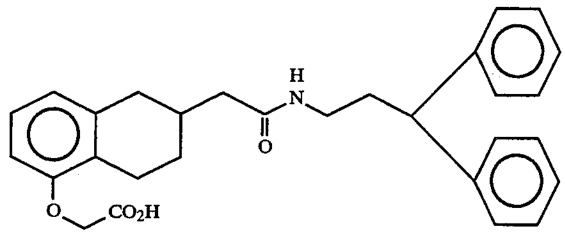 | Rf = 0.25 (CH$_3$OH:CHCl$_3$ = 3:15) | ν 3320, 3027, 2928, 1726, 1583, 1466, 1434, 1230, 1172, 1118, 766, 702. |
| 3(e) | 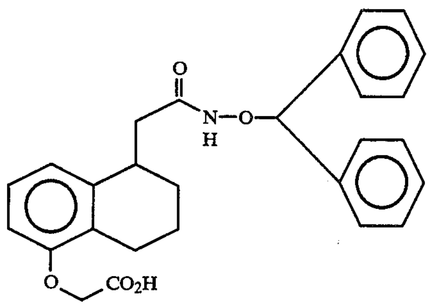 | Rf = 0.18 (CH$_3$OH:CHCl$_3$ = 3:15) | ν 3218, 2943, 1748, 1651, 1580, 1466, 1430, 1246, 1127, 1086, 1021, 770, 701. |
| 3(f) | 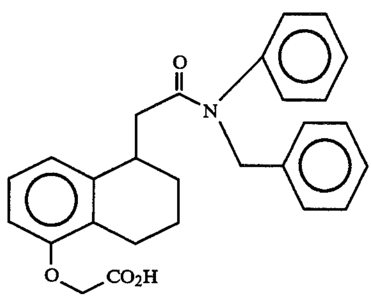 | Rf = 0.13 (CH$_3$OH:CH$_2$Cl$_2$ = 1:9) | ν 2931, 1740, 1606, 1582, 1496, 1464, 1355, 1277, 1208, 1119, 1079, 1016, 780, 702. |
| 3(g) | 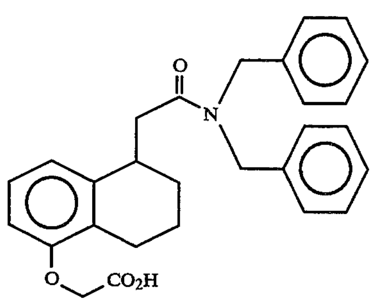 | Rf = 0.13 (CH$_3$OH:CH$_2$Cl$_2$ = 1:9) | ν 2930, 1739, 1582, 1464, 1453, 1360, 1205, 1117, 1077, 1029, 953, 880, 778, 723, 700. |
| 3(h) | 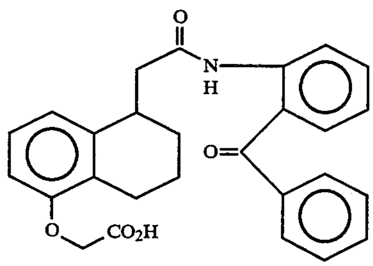 | Rf = 0.13 (CH$_3$OH:CH$_2$Cl$_2$ = 1:9) | ν 2932, 1738, 1636, 1604, 1581, 1520, 1447, 1295, 1263, 1116, 1075, 1045, 924, 879, 753, 701, 641. |

5,344,836

TABLE 4-continued

| Ex. No. | Structure | TLC | IR (cm$^{-1}$) |
|---|---|---|---|
| 3(i) | 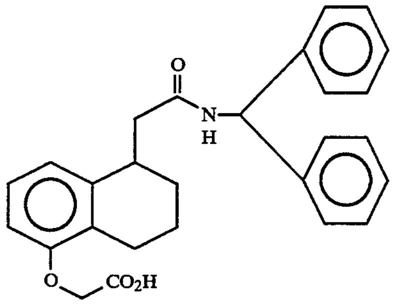 | Rf = 0.09 (CH$_3$OH:CH$_2$Cl$_2$ = 1:9) | ν 3324, 2934, 1749, 1641, 1581, 1534, 1497, 1467, 1428, 1372, 1245, 1126, 918, 783, 740, 699, 640, 560. |
| 3(j) | 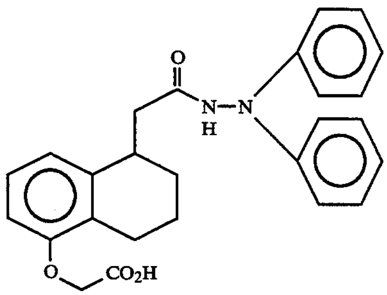 | Rf = 0.09 (CH$_3$OH:CH$_2$Cl$_2$ = 1:9) | ν 3271, 2927, 1741, 1667, 1591, 1495, 1465, 1428, 1331, 1254, 1123, 1077, 917, 774, 746, 689, 624, 559, 503. |
| 3(k) | 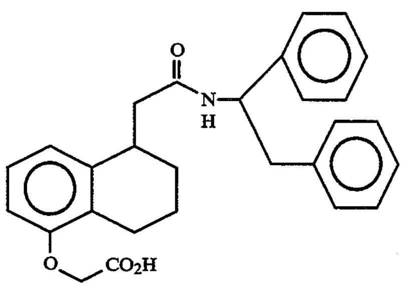 | Rf = 0.09 (CH$_3$OH:CH$_2$Cl$_2$ = 1:9) | ν 3326, 2937, 1745, 1641, 1582, 1538, 1496, 1466, 1430, 1337, 1248, 1124, 918, 757, 699, 540. |
| 3(l) | 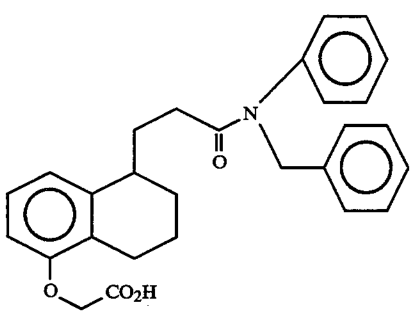 | Rf = 0.32 (CH$_2$Cl$_2$:CH$_3$OH = 9:1) | ν 2930, 1717, 1611, 1584, 1496, 1462, 1330, 1273, 1229, 1145, 1115, 1077, 1018, 877, 781, 701, 559, 434. |
| 3(m) | 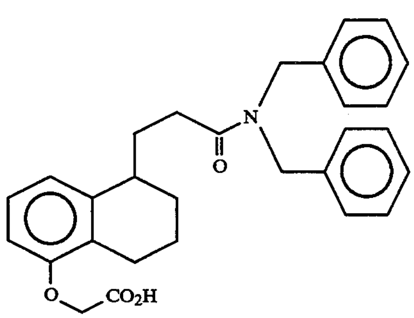 | Rf = 0.32 (CH$_2$Cl$_2$:CH$_3$OH = 9:1) | ν 2931, 1737, 1581, 1496, 1454, 1360, 1207, 1117, 1077, 1029, 953, 776, 731, 700, 456. |

TABLE 4-continued

| Ex. No. | Structure | TLC | IR (cm$^{-1}$) |
|---|---|---|---|
| 3(n) | 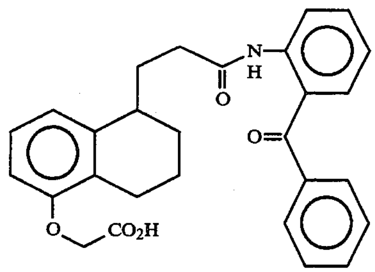 | Rf = 0.32 (CH$_2$Cl$_2$:CH$_3$OH = 9:1) | ν 2934, 1738, 1698, 1636, 1604, 1582, 1520, 1448, 1374, 1264, 1119, 1047, 926, 755, 702, 642. |
| 3(o) | 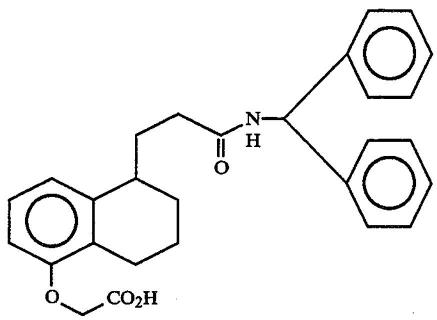 | Rf = 0.24 (CH$_2$Cl$_2$:CH$_3$OH = 9:1) | ν 3316, 2944, 1699, 1643, 1582, 1531, 1494, 1463, 1335, 1332, 1275, 1224, 1121, 1079, 924, 696, 637. |
| 3(p) | 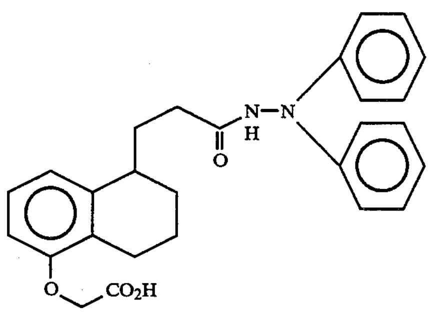 | Rf = 0.20 (CH$_2$Cl$_2$:CH$_3$OH = 9:1) | ν 3278, 2936, 1709, 1667, 1591, 1521, 1497, 1461, 1390, 1335, 1275, 1232, 1122, 1079, 892, 749, 692, 629. |
| 3(q) | 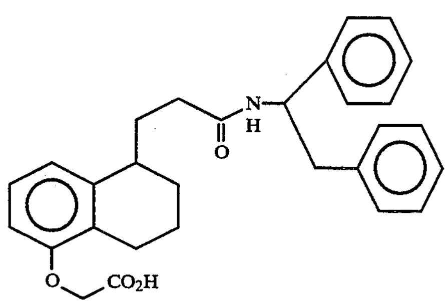 | Rf = 0.32 (CH$_2$Cl$_2$:CH$_3$OH = 9:1) | ν 3321, 3029, 2933, 1707, 1646, 1581, 1537, 1496, 1455, 1338, 1225, 1122, 893, 779, 758, 700, 540. |
| 3(r) | 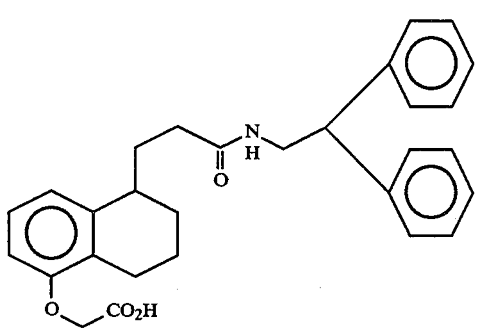 | Rf = 0.32 (CH$_2$Cl$_2$:CH$_3$OH = 9:1) | ν 3340, 2941, 1743, 1641, 1580, 1542, 1496, 1451, 1425, 1340, 1252, 1126, 921, 782, 755, 735, 698, 586, 541. |

TABLE 4-continued

| Ex. No. | Structure | TLC | IR (cm$^{-1}$) |
|---|---|---|---|
| 3(s) | 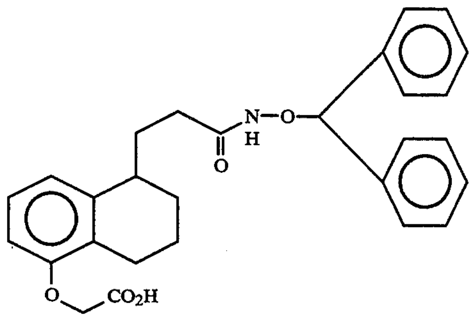 | Rf = 0.20 (CH$_2$Cl$_2$:CH$_3$OH = 9:1) | ν 3179, 2924, 2858, 1723, 1624, 1582, 1496, 1435, 1341, 1245, 1175, 1118, 1069, 985, 887, 774, 758, 744, 724, 694, 595. |
| 3(t) | 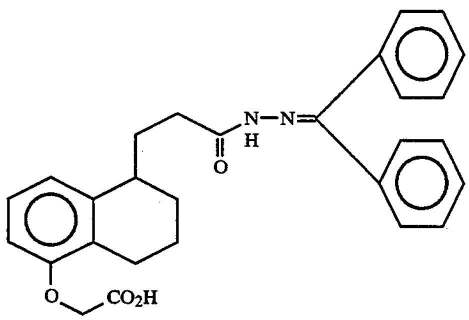 | Rf = 0.32 (CH$_2$Cl$_2$:CH$_3$OH = 9:1) | ν 3267, 2926, 1742, 1642, 1581, 1438, 1392, 1325, 1269, 1234, 1119, 1074, 918, 774, 727, 704, 692, 629. |
| 3(u) | 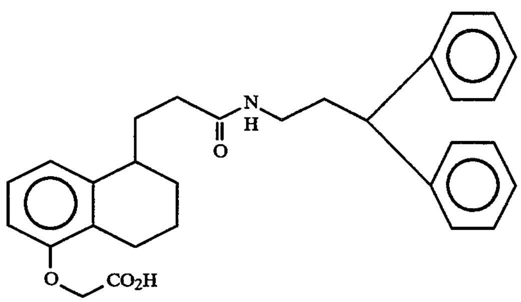 | Rf = 0.24 (CH$_2$Cl$_2$:CH$_3$OH = 9:1) | ν 3339, 3027, 2932, 2867, 1736, 1603, 1581, 1494, 1463, 1340, 1224, 1118, 1031, 886, 774, 752, 702. |
| 3(v) | 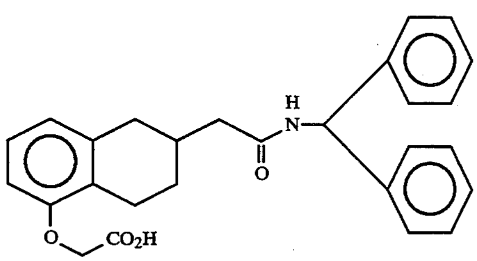 | Rf = 0.09 (CH$_3$OH:CH$_2$Cl$_2$ = 1:9) | ν 3281, 3029, 2923, 1739, 1711, 1646, 1583, 1526, 1494, 1469, 1427, 1343, 1305, 1254, 1124, 921, 769, 743, 699, 563. |
| 3(w) | 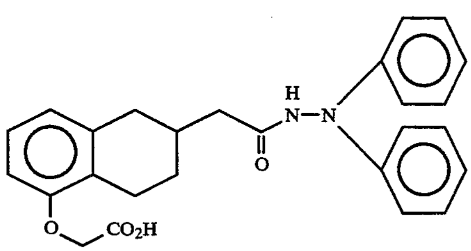 | Rf = 0.06 (CH$_3$OH:CH$_2$Cl$_2$ = 1:9) | ν 3226, 2925, 1737, 1713, 1672, 1590, 1494, 1469, 1253, 1162, 1128, 971, 775, 748, 691, 626, 561. |

TABLE 4-continued

| Ex. No. | Structure | TLC | IR (cm$^{-1}$) |
|---|---|---|---|
| 3(x) | 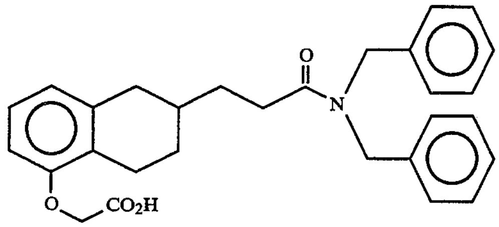 | Rf = 0.12 (CH$_3$OH:CH$_2$Cl$_2$ = 1:9) | ν 3030, 2925, 1737, 1584, 1496, 1466, 1453, 1358, 1207, 1118, 1029, 952, 767, 732, 700. |
| 3(y) | 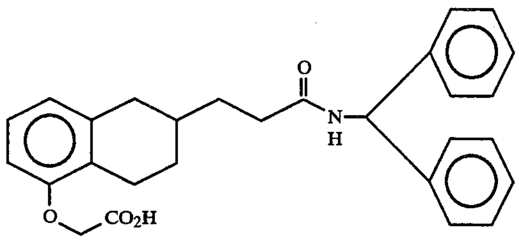 | Rf = 0.09 (CH$_3$OH:CH$_2$Cl$_2$ = 1:9) | ν 3318, 3032, 2931, 1751, 1641, 1584, 1529, 1496, 1468, 1451, 1430, 1344, 1310, 1254, 1123, 984, 912, 768, 734, 696, 642, 553. |
| 3(z) | 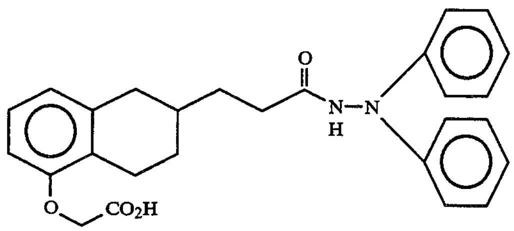 | Rf = 0.06 (CH$_3$OH:CH$_2$Cl$_2$ = 1:9) | ν 3268, 2926, 1734, 1703, 1669, 1585, 1522, 1498, 1464, 1333, 1277, 1231, 1118, 921, 764, 746, 692, 629, 559, 506. |
| 3(aa) | 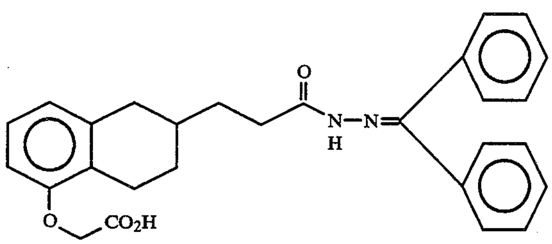 | Rf = 0.09 (CH$_3$OH:CH$_2$Cl$_2$ = 1:9) | ν 3060, 2923, 1737, 1638, 1585, 1466, 1389, 1322, 1215, 1118, 957, 768, 694. |
| 3(bb) | 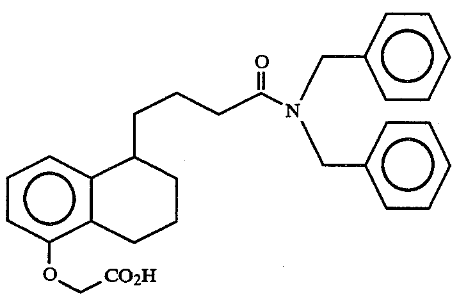 | Rf = 0.12 (CH$_3$OH:CH$_2$Cl$_2$ = 1:9) | ν 2932, 1736, 1580, 1496, 1453, 1300, 1207, 1117, 1079, 1029, 877, 778, 732, 699, 511, 456. |
| 3(cc) | 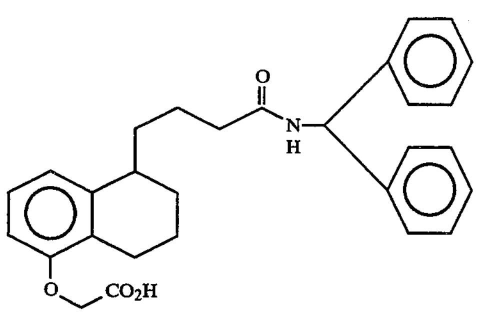 | Rf = 0.09 (CH$_3$OH:CH$_2$Cl$_2$ = 1:9) | ν 3311, 3030, 2932, 1709, 1640, 1582, 1534, 1493, 1465, 1265, 1228, 1177, 1124, 922, 771, 760, 744, 700, 622. |

TABLE 4-continued

| Ex. No. | Structure | TLC | IR (cm$^{-1}$) |
|---|---|---|---|
| 3(dd) | 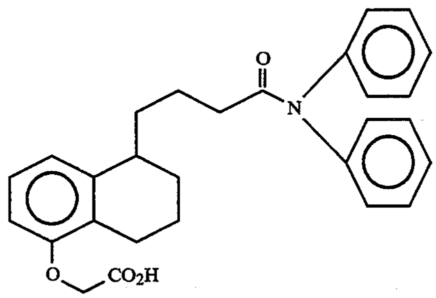 | Rf = 0.15 (CH$_3$OH:CH$_2$Cl$_2$ = 1:9) | ν 3063, 2933, 2863, 1737, 1672, 1620, 1583, 1493, 1462, 1390, 1273, 1117, 1077, 1005, 876, 777, 758, 703, 590. |
| 3(ee) | 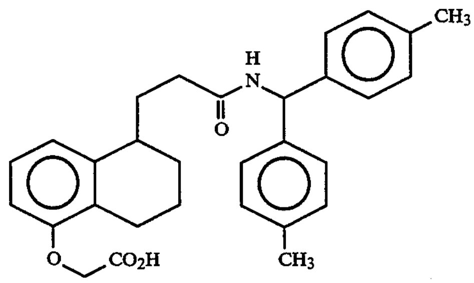 | Rf = 0.24 (CH$_3$OH:CH$_2$Cl$_2$ = 1:9) | ν 3320, 3030, 2935, 1745, 1645, 1583, 1532, 1494, 1350, 1265, 1124, 920, 830. |
| 3(ff) | 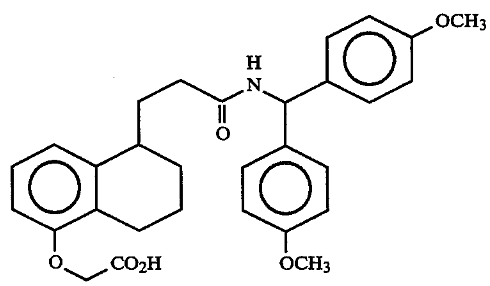 | Rf = 0.24 (CH$_3$OH:CH$_2$Cl$_2$ = 1:9) | ν 3324, 3025, 2940, 2833, 1743, 1045, 1581, 1530, 1495, 1250, 1123, 930, 695. |
| 3(gg) | 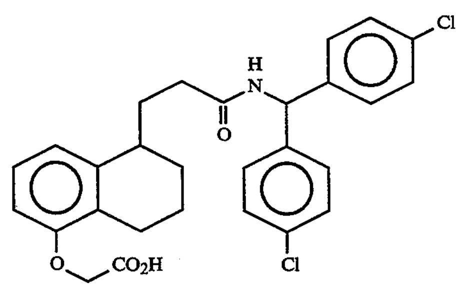 | Rf = 0.24 (CH$_3$OH:CH$_2$Cl$_2$ = 1:9) | ν 3321, 3030, 2932, 1741, 1644, 1582, 1531, 1493, 1260, 1124, 990, 870. |
| 3(hh) | 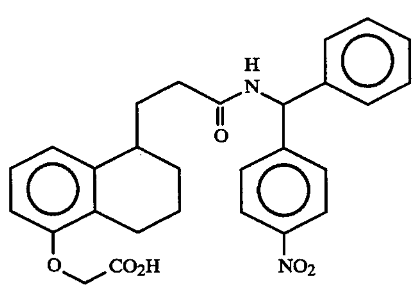 | Rf = 0.22 (CH$_3$OH:CH$_2$Cl$_2$ = 1:9) | ν 3320, 3033, 2916, 1738, 1645, 1582, 1521, 1493, 1253, 1126, 930, 696. |

TABLE 4-continued

| Ex. No. | Structure | TLC | IR (cm$^{-1}$) |
|---|---|---|---|
| 3(ii) | 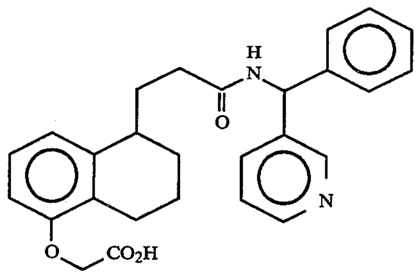 | Rf = 0.13 (CH$_3$OH:CH$_2$Cl$_2$ = 1:9) | ν 3320, 3031, 2472, 1742, 1644, 1531, 1488, 1239, 1119, 930, 701. |
| 3(jj) | 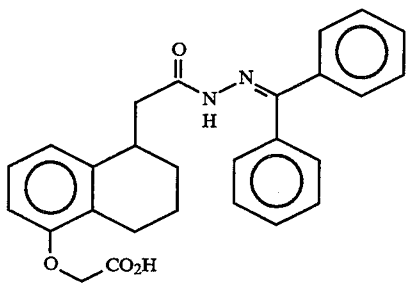 | Rf = 0.25 (MeOH:CHCl$_3$ = 3:17) | ν 3200, 2930, 2539, 1741, 1631, 1586, 1463, 1391, 1221, 1126, 912, 775, 694. |
| 3(kk) | 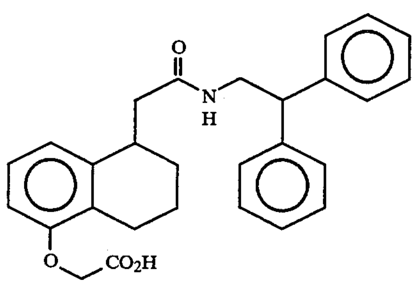 | Rf = 0.25 (MeOH:CHCl$_3$ = 3:17) | ν 3341, 2936, 1742, 1641, 1548, 1466, 1426, 1256, 1126, 917, 630. |
| 3(ll) | 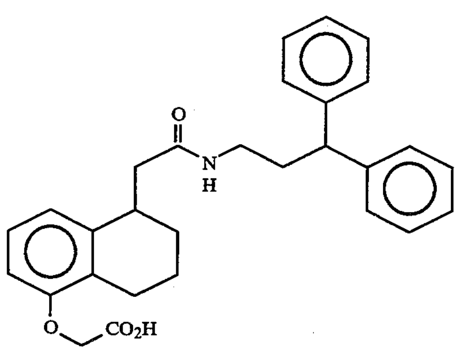 | Rf = 0.25 (MeOH:CHCl$_3$ = 3:17) | ν 3306, 2932, 1734, 1714, 1641, 1580, 1549, 1466, 1426, 1250, 1124, 946, 781, 705. |
| 3(mm) | 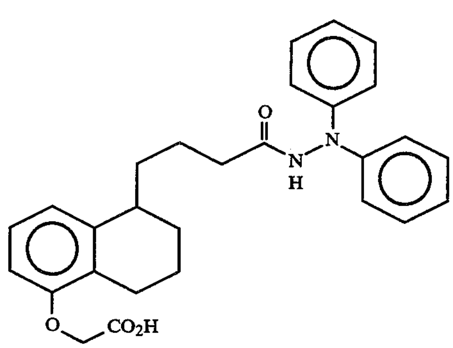 | Rf = 0.06 (MeOH:CH$_2$Cl$_2$ = 1:9) | ν 3273, 2934, 1709, 1671, 1591, 1519, 1496, 1460, 1329, 1275, 1228, 1124, 886, 772, 746, 690, 629. |

TABLE 4-continued

| Ex. No. | Structure | TLC | IR (cm$^{-1}$) |
|---|---|---|---|
| 3(nn) | 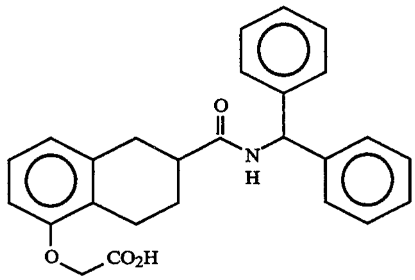 | Rf = 0.30 (MeOH:CH$_2$Cl$_2$ = 1:5) | ν 3317, 3032, 2935, 1745, 1709, 1646, 1604, 1583, 1536, 1495, 1468, 1455, 1430, 1309, 1281, 1243, 1216, 1201, 1128, 1216, 1201, 1128, 1031, 975, 920, 769, 739, 698, 640. |
| 3(oo) | 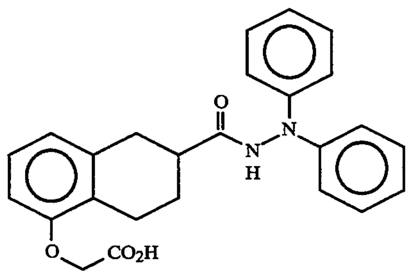 | Rf = 0.28 (MeOH:CH$_2$Cl$_2$ = 1:5) | ν 3272, 3035, 2934, 1743, 1673, 1590, 1496, 1467, 1430, 1332, 1261, 1244, 1183, 1118, 767, 747, 695. |
| 3(pp) | 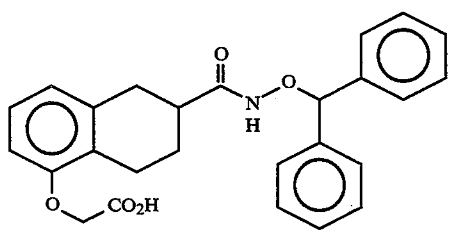 | Rf = 0.35 (MeOH:CH$_2$Cl$_2$ = 1:5) | ν 3234, 3032, 2933, 1736, 1639, 1586, 1495, 1467, 1438, 1215, 1117, 1084, 1033, 974, 914, 876, 848, 763, 745, 701, 651. |
| 3(qq) | 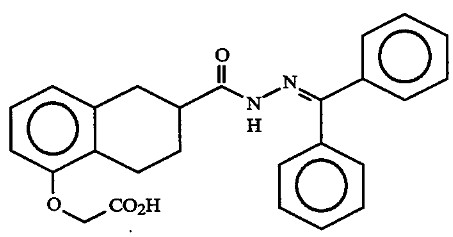 | Rf = 0.33 (MeOH:CH$_2$Cl$_2$ = 1:5) | ν 3311, 3059, 2932, 1737, 1678, 1638, 1586, 1509, 1491, 1467, 1446, 1396, 1341, 1322, 1234, 1214, 1196, 1117, 1077, 1029, 960, 912, 770, 737, 695, 638, 609. |
| 3(rr) | 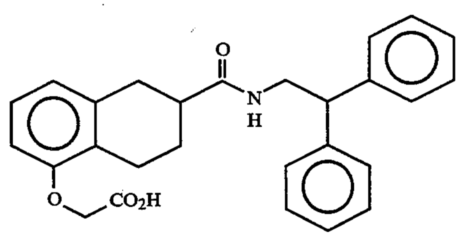 | Rf = 0.35 (MeOH:CH$_2$Cl$_2$ = 1:5) | ν 3369, 3028, 2932, 1737, 1626, 1585, 1544, 1495, 1466, 1214, 1117, 769, 739, 702, 546. |
| 3(ss) | 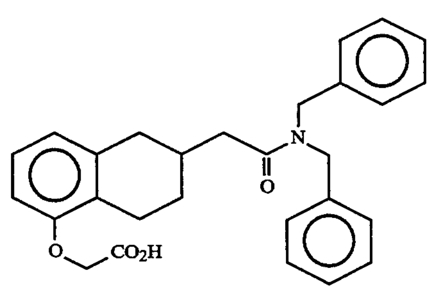 | Rf = 0.12 (MeOH:CH$_2$Cl$_2$ = 1:9) | ν 3032, 2920, 1737, 1584, 1495, 1466, 1453, 1360, 1205, 1117, 1082, 1029, 950, 768, 733, 700, 511. |

The compounds shown in the table 4 are named as follows:

3(a) [2-(Diphenylmethoxyaminocarbonylmethyl)-1,2,3,4-tetrahydronaphthalen-5-yl] oxyacetic acid 3(b) [2-((Diphenylmethylideneamino) aminocarbonylmethyl)-1,2,3,4-tetrahydronaphthalen-5-yl] oxyacetic acid 3(c) [2-((2, 2-Diphenylethyl)aminocarbonylmethyl)-1,2,3,4-tetrahydronaphthalen-5-yl] oxyacetic acid 3(d) [2-((3, 3-Diphenylpropyl) aminocarbonyimethyl)-1,2,3,4-tetrahydronaphthalen-5-yl] oxyacetic acid 3(e) [1-(Diphenylmethoxyaminocarbonylmethyl)-1,2,3,4-tetrahydronaphthalen-5-yl] oxyacetic acid 3(f) [1-((N-Benzyl-N-phenylamino) carbonylmethyl)-1,2,3,4-tetrahydronaphthalen-5-yl] oxyacetic acid 3(g) [1 -(Dibenzylaminocarbonylmethyl)-1,2,3,4-tetrahydronaphthalen-5-yl] oxyacetic acid 3(h) [1-((2-Benzoylphenyl) aminocarbonylmethyl)-1,2,3,4-tetrahydronaphthalen-5-yl] oxyacetic acid 3(i) [1-(Diphenylmethylaminocarbonylmethyl)-1,2,3,4-tetrahydronaphthalen-5-yl] oxyacetic acid 3(j) [1-((N, N-Diphenylamino) aminocarbonylmethyl)-1,2,3,4-tetrahydronaphthalen-5-yl] oxyacetic acid 3(k) [1-((1,2-Diphenylethyl) aminocarbonylmethyl)-1,2,3,4-tetrahydronaphthalen-5-yl] oxyacetic acid 3(l) [1-(2-(N-Benzyl-N-phenylamino) carbonylethyl)-1,2,3,4-tetrahydronaphthalen-5-yl] oxyacetic acid 3(m) [1-( 2-Dibenzylaminocarbonylethyl)-1,2,3,4-tetrahydronaphthalen-5-yl] oxyacetic acid 3(n) [1-(2-(2-Benzoylphenyl) aminocarbonylethyl)-1,2,3,4-tetrahydronaphthalen-5-yl] oxyacetic acid 3(o) [1-(2-Diphenylmethylaminocarbonylethyl)-1,2,3,4-tetrahydronaphthalen-5-yl] oxyacetic acid 3(p) [1-(2-(N, N-Diphenylamino) aminocarbonylethyl)-1,2,3,4-tetrahydronaphthalen-5-yl] oxyacetic acid 3(q) [1-(2-(1,2-Diphenylethyl) aminocarbonylethyl)-1,2,3,4-tetrahydronaphthalen-5-yl] oxyacetic acid 3(r) [1-(2-(2,2-Diphenylethyl) aminocarbonylethyl)-1,2,3,4-tetrahydronaphthalen-5-yl] oxyacetic acid 3(s) [1-(2-Diphenylmethoxyaminocarbonylethyl)-1,2,3,4-tetrahydronaphthalen-5-yl] oxyacetic acid 3(t) [1-(2-(Diphenylmethylideneamino) aminocarbonylethyl)-1,2,3,4-tetrahydronaphthalen-5-yl] oxyacetic acid 3(u) [1-(2-(3,3-Diphenylpropyl) aminocarbonylethyl)-1,2,3,4-tetrahydronaphthalen-5-yl] oxyacetic acid 3(v) [2-(Diphenylmethylaminocarbonylmethyl)-1,2,3,4-tetrahydronaphthalen-5-yl] oxyacetic acid 3(w) [2-((N, N-Diphenylamino) aminocarbonylmethyl)-1,2,3,4-tetrahydronaphthalen-5-yl] oxyacetic acid 3(x) [2-(2-(N, N-Dibenzylamino) carbonylethyl)-1,2,3,4-tetrahydronaphthalen-5-yl] oxyacetic acid 3(y) [2-( 2-(Diphenyl methylamino) carbonylethyl)-1,2,3,4-tetrahydronaphthalen-5-yl] oxyacetic acid 3(z) [2-(2-(N, N-Diphenylamino) aminocarbonylethyl)-1,2,3,4-tetrahydronaphthalen-5-yl] oxyacetic acid 3(aa) [2-(2-(Diphenylmethylideneamino) aminocarbonylethyl)-1,2,3,4-tetrahydronaphthalen-5-yl] oxyacetic acid 3(bb) [1-(3-(N, N-Dibenzylamino) carbonylpropyl)-1,2,3,4-tetrahydronaphthalen-5-yl] oxyacetic acid 3(cc) [1-(3-Diphenylmethylaminocarbonylpropyl)-1,2,3,4-tetrahydronaphthalen- 5-yl] oxyacetic acid 3(dd) [1-(3-(N, N-Diphenylamino)carbonylpropyl)-1,2,3,4-tetrahydronaphthalen-5-yl] oxyacetic acid 3(ee) [1-(2-Bis (4-methylphenyl) methylaminocarbonylethyl)-1,2,3,4-tetrahydronaphthalen-5-yl] oxyacetic acid 3(ff) [1-(2-Bis (4-methoxyphenyl) methylaminocarbonylethyl)-1,2,3,4-tetrahydronaphthalen-5-yl] oxyacetic acid 3(gg) [1-(2-Bis (4-chlorophenyl) methylaminocarbonylethyl)-1,2,3,4-tetrahydronaphthalen-5-yl] oxyacetic acid 3(hh) [1-(2-(1-(4-Nitrophenyl)-1-phenylmethyl) aminocarbonylethyl)-1,2,3,4-tetrahydronaphthalen-5-yl] oxyacetic acid 3(ii) [1-(2-(1-(3-Pyridyl)-1-phenylmethyl) aminocarbonylethyl)-1,2,3,4-tetrahydronaphthalen-5-yl] oxyacetic acid 3(jj) [1-((Diphenylmethylideneamino) aminocarbonylmethyl)-1,2,3,4-tetrahydronaphthalen-5-yl] oxyacetic acid 3(kk) [1-((2, 2-Diphenylethyl) aminocarbonylmethyl)-1,2,3,4-tetrahydronaphthalen-5-yl] oxyacetic acid 3(ll) [1-((3, 3-Diphenylpropyl) aminocarbonylmethyl)-1,2,3,4-tetrahydronaphthalen-5-yl] oxyacetic acid 3(mm) [1-(3-(N, N-Diphenylamino) aminocarbonylpropyl)-1,2,3,4-tetrahydronaphthalen-5-yl] oxyacetic acid 3(nn) [2-(Diphenylmethylaminocarbonyl)-1,2,3,4-tetrahydronaphthalen-5-yl] oxyacetic acid 3(oo) [2-((N, N-Diphenylamino) aminocarbonyl)-1,2,3,4-tetrahydronaphthalen-5-yl] oxyacetic acid 3(pp) [2-(Diphenylmethoxyaminocarbonyl)-1,2,3,4-tetrahydronaphthalen-5-yl] oxyacetic acid 3(qq) [2-((Diphenylmethylideneamino) aminocarbonyl)-1,2,3,4-tetrahydronaphthalen-5-yl] oxyacetic acid 3(rr) [2-((2, 2-Diphenylethyl) aminocarbonyl)-1,2,3,4-tetrahydronaphthalen-5-yl] oxyacetic acid 3(ss) [2-((N, N-Dibenzylamino) carbonylmethyl)-1,2,3,4-tetrahydronaphthalen-5oyl] oxyacetic acid

EXAMPLE 4

Methyl [2-((N,N-diphenylamino) methylcarbonylaminomethyl)-1,2,3,4-tetrahydronaphthalen-5-yl] oxyacetate

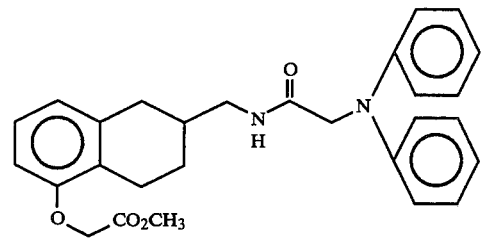

By the same procedure as example 1 (using N, N-diphenylglycine instead of dibenzylamine), using the compound prepared in reference example 3, the title compound having the following physical data was given.

TLC: Rf 0.29 (ethyl acetate:hexane=2:3);

IR (cm$^{-1}$): ν 3253, 3088, 2922, 2359, 1760, 1741, 1653, 1587, 1499, 1464, 1369, 1255, 1214, 1114, 1006, 864, 747, 706, 691.

EXAMPLE 4(a)

By the same procedure as example 4, using the compound prepared in reference example 4, the compound having the following physical data shown in the table 5 was given.

TABLE 5

| Ex. No. | Structure | TLC | IR (cm$^{-1}$) |
|---|---|---|---|
| 4 (a) | 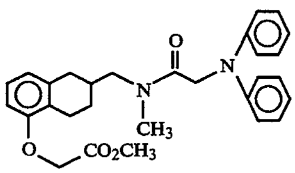 | Rf = 0.40 (CH$_3$CO$_2$C$_2$H$_5$:n-C$_6$H$_{14}$ = 4:6) | $\nu$ 2934, 2361, 1752, 1657, 1588, 1500, 1366, 1208, 1125, 994, 861, 810, 769, 744, 692. |

The compound shown in the table 5 is named as follows:

4(a) Methyl [2-((N-methyl-N-(diphenylaminomethylcarbonyl) amino) methyl)-1,2,3,4-tetrahydronaphthalen-5-yl] oxyacetate

EXAMPLE 5

[2-(2, 2-Diphenylethylcarbonylaminomethyl)-1,2,3,4tetrahydronaphthalen-5-yl] oxyacetic acid

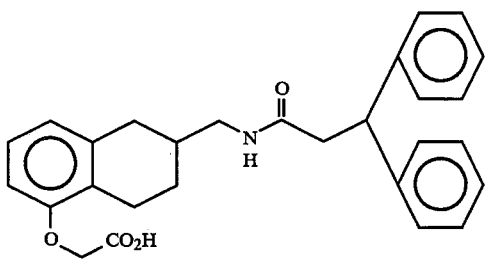

By the same procedure as example 1 (using benzhydrylacetic acid instead of dibenzylamine)→example 2, using the compound prepared in reference example 3, the title compound having the following physical data was given.

TLC: Rf 0.25 (methanol:methylene chloride=3:17);
IR(cm$^{-1}$): $\nu$ 3384, 3025, 2923, 2355, 1909, 1732, 1582, 1497, 1463, 1366, 1214, 1133, 967, 895, 749, 695.

EXAMPLE 6

Methyl [2-(N-methyl-N-(diphenylmethylaminocarbonyl) aminomethyl)-1,2,3,4-tetrahydronaphthalen-5-yl] oxyacetate

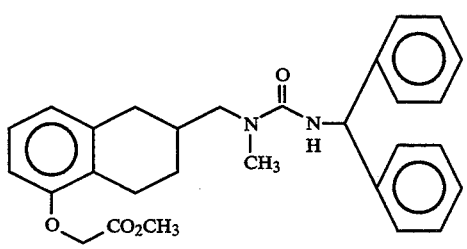

To a solution of the compound prepared in reference example 4 (0.10 g) and triethylamine (0.39 g) in methylene chloride (8.0 ml) was added dropwise a solution of benzhydrylisocyanate (0.10 g) in methylene chloride (3.0 ml) at room temperature. The mixture was stirred for 1 h at room temperature. The mixture was concentrated under reduced pressure. The residue was purified by silica gel column chromatography (ethyl acetate:methylene chloride=1:10) to give the title compound (0.14 g) having the following physical data.

TLC: Rf 0.48 (ethyl acetate:methylene chloride=1:10);
NMR: $\delta$ 7.4~7.2(10H, m), 7.03(1H, t, J=7.5 Hz), 6.70(1H, d, J=7.5 Hz), 6.50(1H, d, J=7.5 Hz), 6.15(1H, d, J=7.0 Hz), 4.93(1H, d, J=7.0 Hz), 4.64(2H, s), 3.80(3H, s), 3.31 (2H, m), 2.99(3H, s), 3.0~2.4(5H, m), 2.0(2H, m), 1.6~1.1(2H, m).

EXAMPLE 7

[2-(N-Methyl-N-(diphenylmethylaminocarbonyl) aminomethyl)-1,2,3,4-tetrahydronaphthalen-5-yl] oxyacetic acid

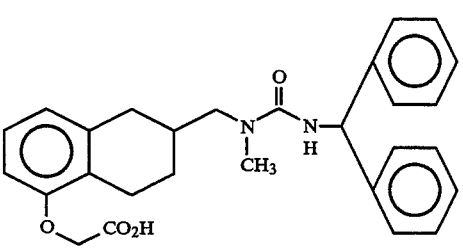

By the same procedure as example 2, using the compound prepared in example 6, the title compound having the following physical data was given.

TLC: Rf 0.24 (methanol:methylene chloride=1:10);
IR(cm$^{-1}$): $\nu$ 3437, 2922, 2362, 1736, 1585, 1510, 1466, 1211, 1117, 766, 700.

EXAMPLE 8

[2-((N-Methyl-N-(2, 2-diphenylethyl) carbonylamino) methyl)-1,2,3,4-tetrahydronaphthalen-5-yl] oxyacetic acid

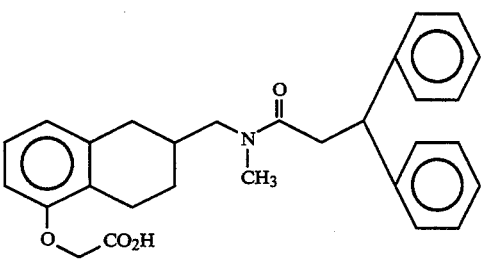

By the same procedure as example 5, using the compound prepared in reference example 4, the title compound having the following physical data was given.

TLC: Rf 0.25 (methanol:methylene chloride=3:17);
IR(cm$^{-1}$): $\nu$ 2921, 2355, 1734, 1582, 1494, 1464, 1350, 1276, 1219, 1111, 1084, 873, 765, 703, 607.

EXAMPLE 8(a)~8(d)

By the same procedure as example 1 (using N-phenyl-N-benzylglycine in example 8(b) and example 8(d) instead of N, N-diphenylglycine)→example 2, the compounds shown in the following table 6 were given by using the compound prepared in reference example 4 or by using the compound obtained from the compound prepared in reference example 1 by the same procedure as reference example 4 (using propylamine instead of methylamine).

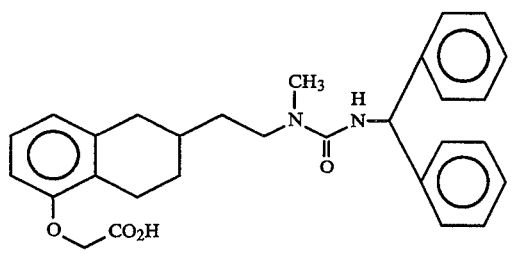

TABLE 6

| Ex. No. | Structure | TLC | IR (cm⁻¹) |
| --- | --- | --- | --- |
| 8 (a) | 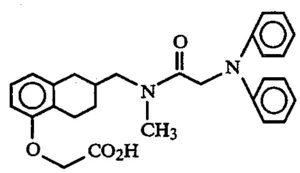 | Rf = 0.28 (CH₂Cl₂:CH₃CO₂C₂H₅ = 1:9) | ν 2926, 1736, 1588, 1499, 1466, 1370, 1229, 1114, 862, 750, 693. |
| 8 (b) | 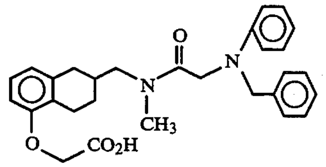 | Rf = 0.42 (CH₃OH:CH₂Cl₂ = 1:4) | ν 3026, 2913, 1766, 1630, 1596, 1506, 1467, 1434, 1399, 1344, 1316, 1263, 1226, 1181, 1112, 1083, 1029, 985, 962, 945, 916, 849, 823, 767, 747, 724, 699, 640, 610, 583, 512, 455. |
| 8 (c) | 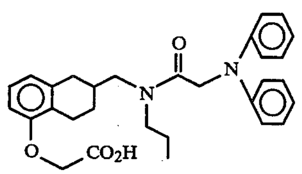 | Rf = 0.46 (CH₃OH:CH₂Cl₂ = 1:4) | ν 3437, 3036, 2927, 1762, 1656, 1605, 1588, 1499, 1466, 1437, 1368, 1343, 1308, 1260, 1228, 1113, 992, 862, 815, 767, 750, 963. |
| 8 (d) | 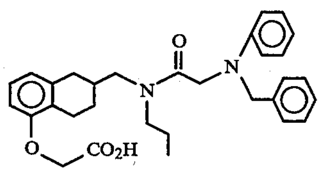 | Rf = 0.50 (CH₃OH:CH₂Cl₂ = 1:4) | ν 3437, 3036, 2927, 1762, 1656, 1605, 1588, 1499, 1466, 1437, 1368, 1343, 1308, 1260, 1228, 1113, 767, 750, 693. |

The compounds shown in the table 6 are named as follows:

8(a) [2-((N-methyl-N-(diphenylaminomethylcarbonyl) amino) methyl)-1,2,3,4-tetrahydronaphthalen-5-yl] oxyacetic acid 8(b) [2-((N-Methyl-N-((N'-benzyl-N'-phenylamino)methylcarbonyl) amino) methyl)-1,2,3,4-tetrahydronaphthalen-5-yl] oxyacetic acid 8(c) [2-((N-Propyl-N-(diphenylaminomethylcarbonyl) amino) methyl)-1,2,3,4-tetrahydronaphthalen-5-yl] oxyacetic acid 8(d) [2-((N-Propyl-N-((N'-benzyl-N'-phenylamino) methylcarbonyl) amino) methyl)-1,2,3,4-tetrahydronaphthalen-5-yl] oxyacetic acid

EXAMPLE 9

[2-(2-(N-Methyl-N-(diphenylmethylamino)carbonylamino) ethyl)-1,2,3,4-tetrahydronaphthalen-5-yl] oxyacetic acid By the same procedure as reference example 1→reference example 4→example 6→example 2, using methyl [2-(2-hydroxyethyl)-1,2,3,4-tetrahydronaphthalen-5-yl] oxyacetate instead of methyl (1-hydroxymethyl-1,2,3,4-tetrahydronaphthalen-5-yl) oxyacetate, the title compound having the following physical data was given.

TLC: Rf 0.19 (methanol:methylene chloride=1:9);

IR(cm⁻¹): ν 3395, 3062, 2921, 2362, 2344, 1737. 1604, 1585, 1516, 1466, 1210, 1118, 1028, 765, 743, 701, 608.

EXAMPLE 10

[2-(2-(N-Methyl-N-(N'-phenyl-N'-benzylamino) methylcarbonylamino) ethyl)-1,2,3,4-tetrahydronaphthalen-5-yl] oxyacetic acid

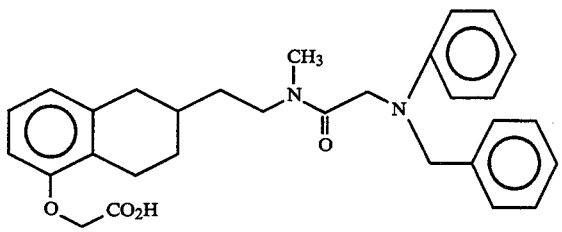

By the same procedure as reference example 1→reference example 4→example 1 (using N-phenyl-N-benzylglycine instead of dibenzylamine)→example 2, using methyl [2-(2-hydroxyethyl)-1,2,3,4-tetrahydronaphthalen-5-yl] oxyacetate instead of methyl (1-hydroxymethyl-1,2,3,4-tetrahydronaphthalen-5-yl) oxyacetate, the title compound having the following physical data was given.

TLC: Rf 0.43 (methanol:methylene chloride=1:4);
IR(cm$^{-1}$): ν 2923, 1736, 1600, 1507, 1466, 1349, 1232, 1117, 990, 749, 694.

EXAMPLE 10(a)~10(c)

By the same procedure as example 10 (proviso that the corresponding proper compounds were used instead of methylamine in reference example 4 and N-phenyl-N-benzylglycine in example 1, respectively), the compounds shown in table 7 were given.

10(a) [2-(2-(N-Propyl-N-(diphenylaminomethylcarbonyl) amino) ethyl)-1,2,3,4-tetrahydronaphthalen-5-yl] oxyacetic acid 10(b) [2-(2-(N-Propyl-N-((N'-benzyl-N'-phenylaminol) methylcarbonyl) amino) ethyl)-1,2,3,4-tetrahydronaphthalen-5-yl] oxyacetic acid 10(c) [2-(2-(N-Methyl-N-(diphenylaminomethylcarbonyl) amino) ethyl)-1,2,3,4-tetrahydronaphthalen-5-yl] oxyacetic acid

EXAMPLE 11

[2-((N-Methyl-N-(diphenylmethylaminothiocarbonyl) amino) methyl)-1,2,3,4-tetrahydronaphthalen-5-yl] oxyacetic acid

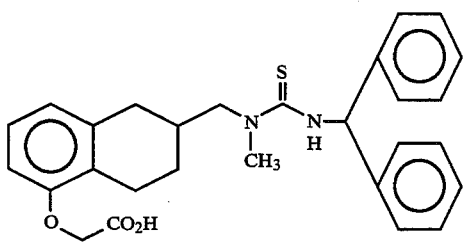

By the same procedure as example 6 (using benzhydrylthioisocyanate instead of benzhydrylisocyanate)-→example 2, using the compound prepared in reference example 4, the title compound having the following

TABLE 7

| Ex. No. | Structure | TLC | IR (cm$^{-1}$) |
|---|---|---|---|
| 10(a) | 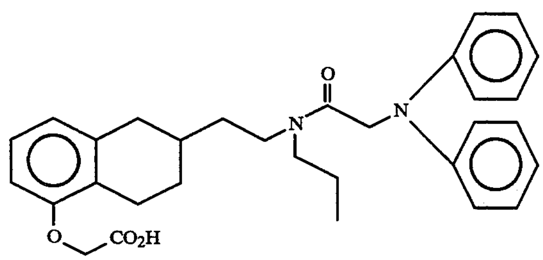 | Rf = 0.54 (CH$_3$OH:CH$_2$Cl$_2$ = 1:4) | ν 3500, 2927, 1762, 1605, 1588, 1499, 1466, 1369, 1343, 1229, 1117, 863, 750, 694. |
| 10(b) | 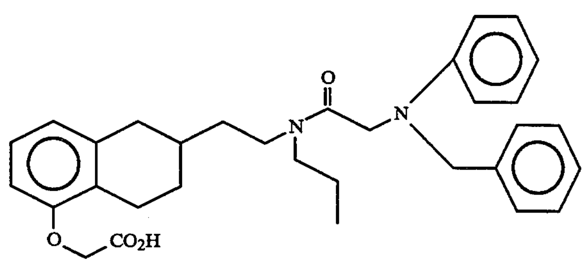 | Rf = 0.54 (CH$_3$OH:CH$_2$Cl$_2$ = 1:4) | ν 3500, 3029, 2926, 1741, 1600, 1507, 1466, 1349, 1229, 1118, 749, 694. |
| 10(c) | 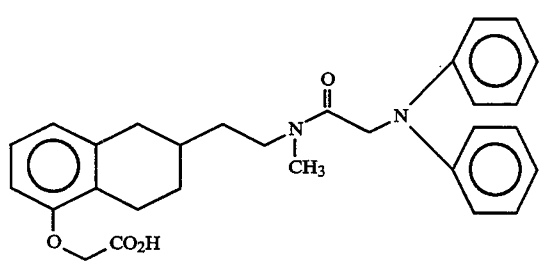 | Rf = 0.52 (CH$_3$OH:CH$_2$Cl$_2$ = 1:4) | ν 3436, 2923, 1736, 1605, 1588, 1499, 1466, 1368, 1263, 1229, 1117, 862, 750, 694. |

The compounds shown in the table 7 are named as follows:

physical data was given.

TLC: Rf 0.20 (methanol:methylene chloride=1:9);

IR(cm⁻¹): ν 3421, 2921, 2361, 1734, 1601, 1585, 1521, 1466, 1342, 1267, 1235, 1194, 1112, 910, 769, 745, 699.

EXAMPLE 12

[2-(2-(N-Methyl-N-(diphenylmethylaminothiocarbonyl) amino) ethyl)-1,2,3,4-tetrahydronaphthalen-5-yl] oxyacetic acid

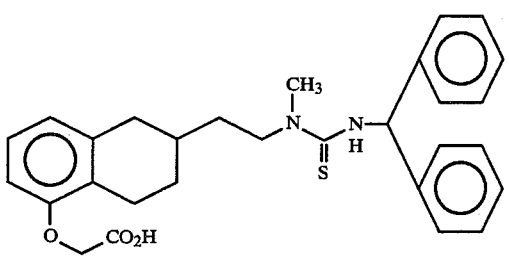

By the same procedure as reference example 1→reference example 4→example 6→example 2, using methyl [2-(2-hydroxyethyl)-1,2,3,4-tetrahydronaphthalen-5-yl] oxyacetate instead of methyl (1-hydroxymethyl-1,2,3,4-tetrahydronaphthalen-5-yl) oxyacetate, the title compound having the following physical data was given.

TLC: Rf 0.20 (methanol:methylene chloride=1:9);

IR(cm⁻¹): ν 3421, 2921, 2361, 1734, 1601, 1585, 1521, 1466, 1342, 1267, 1235, 1194, 1112, 910, 769, 745, 699.

EXAMPLE 13

Methyl [2-(4,4-diphenylsemicarbazonomethyl)-1,2,3,4-tetrahydronaphthalen-5-yl] oxyacetate

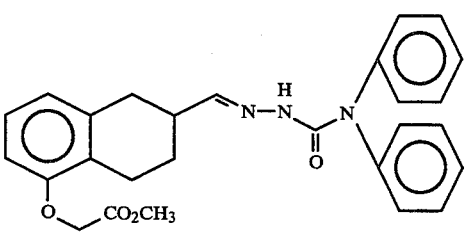

To a solution of methyl (2-formyl-1,2,3,4-tetrahydronaphthalen-5-yl) oxyacetate (248 mg), prepared by the same procedure as reference example 1, in ethanol (10 ml) was added 4,4-diphenylsemicarbazide (0.27 g) under an atmosphere of argon. After stirred for 1 h at room temperature, the mixture was concentrated under reduced pressure. The residue was purified by silica gel column chromatography (methanol:methylene chloride=3:100) to give the title compound (444 mg) having the following physical data.

NMR: δ 7.55(1H, s), 7.5~7.2(10H, m), 7.15(1H, d, J=5 Hz), 7.05(1H, t, J=7.5 Hz), 6.74(1H, d, J=7.5 Hz), 6.53(1H, d, J=7.5 Hz), 4.62(2H, s), 3.80(3H, s), 3.1~2.8(2H, m), 2.8~2.5(3H, m), 2.2~2.0(1H, m), 1.7~1.5(1 H, m).

EXAMPLE 14

[2-(4,4-Diphenylsemicarbazonomethyl)-1,2,3,4-tetrahydronaphthalen-5-yl] oxyacetic acid

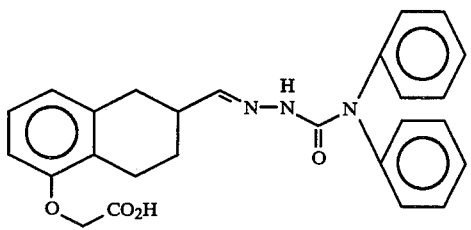

By the same procedure as example 2, using the compound prepared in example 13, the title compound having the following physical data was given.

TLC: Rf 0.29(methanol:methylene chloride=1:4);

IR(cm⁻¹): ν 3425, 3062, 2927, 1670, 1587, 1523, 1492, 1466, 1421, 1377, 1301, 1267, 1216, 1100, 759, 710.

EXAMPLE 14 (a)

[2-(2-(4,4-Diphenylsemicarbazono) ethyl)-1,2,3,4-tetrahydronaphthalen-5-yl] oxyacetic acid

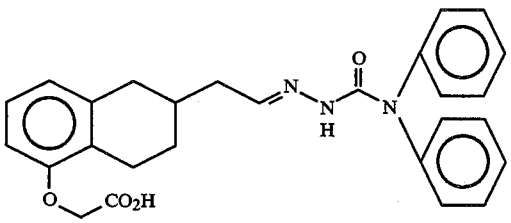

By the same procedure as reference example 1→example 13→example 2, using methyl [2-(2-hydroxyethyl)-1,2,3,4-tetrahydronaphthalen-5-yl] oxyacetate instead of methyl (1-hydroxymethyl-1,2,3,4-tetrahydronaphthalen-5-yl) oxyacetate, the title compound having the following physical data was given.

TLC: Rf 0.28(methanol:methylene chloride=1:4);

IR(cm⁻¹): ν 3415, 3037, 2923, 1672, 1586, 1523, 1492, 1466, 1422, 1367, 1302, 1272, 1107, 759, 701.

EXAMPLE 15

Methyl [2-((4,4-diphenylsemicarbazido) methyl)-1,2,3,4-tetrahydronaphthalen-5-yl] oxyacetate

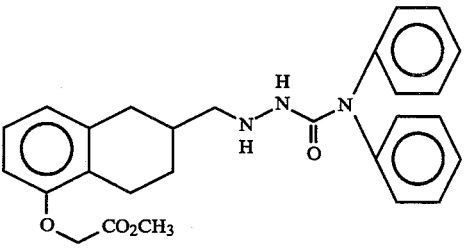

To a solution of the compound prepared in example 13 (291 mg) in methanol (6.5 ml) was added sodium cyanoborohydride (42 mg) and added dropwise followed by acetic acid (1.45 ml). The mixture was stirred overnight at room temperature. After acidified by adding 2N hydrochloric acid until pH 1, the mixture was stirred for 30 min. The mixture was diluted with water. After neutralized by adding sodium bicarbonate until pH 7~8, the mixture was extracted with ethyl acetate. The extract was washed with a saturated aqueous solution of sodium chloride, dried over anhydrous magnesium sulfate, and evaporated. The residue was purified by silica gel column chromatography (ethyl acetate:-hexane=1:1) to give the title compound (235 mg) having the following physical data.

NMR: δ 7.4~7.2 (10H, m), 7.03(1H, t, J=7.5 Hz), 6.72(1H, d, J=7.5 Hz), 6.50(1H, d, J=7.5 Hz), 6.05(1H, s), 4.62(2H, s), 3.80(3H, s), 3.0~2.8(4H, m), 2.7~2.4(2H, m), 2.1~1.7(1H, m), 1.7~1.3(2H, m).

EXAMPLE 16

Methyl [2-((1-methyl-4,4-diphenylsemicarbazido) methyl)-1,2,3,4-tetrahydronaphthalen-5-yl] oxyacetate

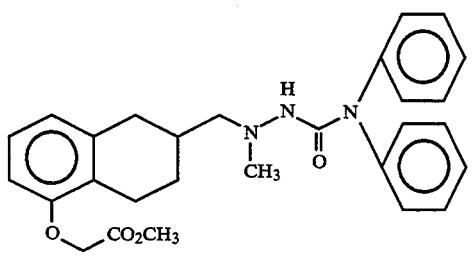

To a suspension of sodium hydride (6.1 mg) in tetrahydrofuran (1.5 ml) was added a solution of the compound prepared in example 15 (70 mg) in tetrahydrofuran (3 ml) under an atmosphere of argon. The mixture was stirred for 30 min at room temperature. To the mixture were successively added methyl iodide (261 mg) and hexamethylphosphoramide (1 ml). After stirred for 2 h at room temperature, the mixture was diluted with ethyl acetate and water. The mixture was extracted with ethyl acetate. The extract was washed with water and a satureted aqueous solution of sodium chloride, successively, dried over anhydrous magnesium sulfate and evaporated. The residue was purified by silica gel column chromatography (ethyl acetate:-hexane=2:3) to give the title compound (27 mg) having the following physical data.

TLC: Rf 0.22 (ethyl acetate:hexane=1:1);
IR(cm$^{-1}$): ν 3306, 2925, 1761, 1692, 1586, 1492, 1467, 1298, 1261, 1208, 1118, 760, 696.

EXAMPLE 17

[2-((1-Methyl-4,4-diphenyisemicabazido) methyl)-1,2,3,4-tetrahydronaphthalen-5-yl] oxyacetic acid

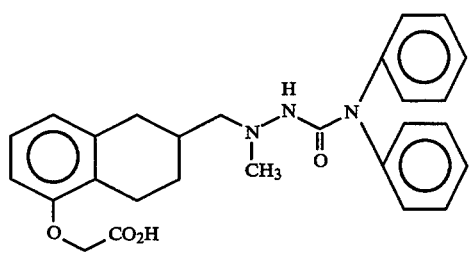

By the same procedure as example 2, using the compound prepared in example 16, the title compound having the following physical data was given.

TLC: Rf 0.24 (methanol:methylene chloride=1:4);
IR(cm$^{-1}$): ν 3424, 2925, 1678, 1587, 1492, 1466, 1300, 1260, 1106, 758, 696.

EXAMPLE 17 (a)

2-(2-( 1-Methyl-4,4-diphenylsemicarbazido) ethyl)-1,2,3,4-tetrahydronaphthalen-5-yl] oxyacetic acid

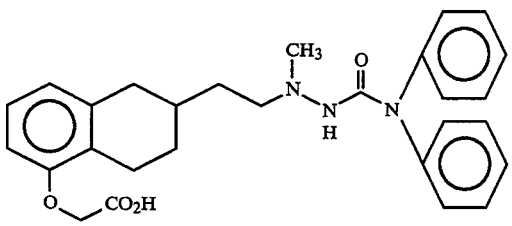

By the same procedure as reference example 1→example 13→example 15→example 16→example 2, using methyl [2-(2-hydroxyethyl)-1,2,3,4-tetrahydronaphthalen-5-yl] oxyacetate instead of methyl (1-hydroxymethyl-1,2,3,4-tetrahydronaphthalen-5-yl) oxyacetate, the title compound having the following physical data was given.

TLC: Rf 0.24 (methanol:methylene chloride=1:4);
IR(cm$^{-1}$): ν 3423, 3062, 2923, 1675, 1587, 1492, 1466, 1301, 1267, 1108, 887, 759, 696, 627.

REFERENCE EXAMPLE 5

Methyl [1-(2E-carboxyvinyl)-1,2,3,4-tetrahydronaphthalen-5-yl] oxyacetate

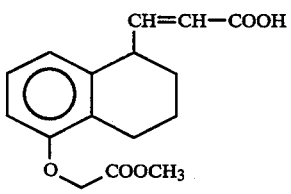

To a solution of isopropylamine (1.87 ml) in dry tetrahydrofuran (50 ml) was added dropwise 1.15M n-butyllithium in hexane solution, (10.6 ml) at −78° C. The mixture was stirred for 20 min at −78° C. to give lithium diisopropylamide. To the obtained lithium diisopropylamide solution was added a solution of dimethyl carboxymethylphosphonate (1.02 g) in dry tetrahydrofuran (3 ml) at −78° C. After stirred for 10 min, to the mixture was added the aldehyde compound (prepared in reference example 1, 1.38 g) at room temperature. The mixture was stirred for 1 h at room temperature. After acidified by adding 1N hydrochloric acid until pH 3, the mixture was extracted with ethyl acetate. The extract was washed with water and a saturated aqueous solution of sodium chloride, successively, dried over anhydrous magnesium sulfate, and evaporated. The residue was crystallized from ethyl acetate-hexane (3:7) to give the title compound (1.07 g) as white powder having the following physical data.

NMR: δ 7.10(1H, dd), 7.06(1H, t), 6.71(1H, d), 6.57(1H, d), 5.76(1H, d), 4.64(2H, s), 3.80(3H, s), 3.66(1 H, m), 2.76(2H, m), 2.00~1.60(4H, m).

EXAMPLE 18

Methyl [1-(2-((N,N-diphenylamino)carbamoyl)-1E-ethylidene)-1,2,3,4-tetrahydronaphthalen-5-yl] oxyacetate

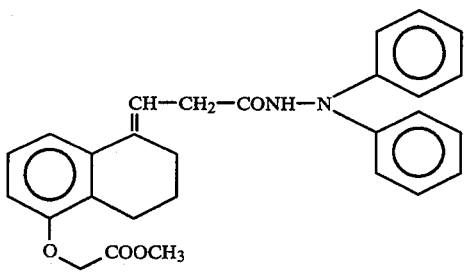

A solution of the carboxylic acid (prepared in reference example 5, 150 mg), 2-chloro-N-methylpyridinum iodide (197 mg). 1,1-diphenylhydrazine hydrochloride (147 mg) and triethylamine (0.216 ml) in methylene chloride (6 ml) was stirred overnight at room temperature. The mixture was poured into 1N hydrochloric acid, and extracted with methylene chloride. The extract was washed with a saturated aqueous solution of sodium chloride, dried over anhydrous magnesium sulfate, and evaporated. The residue was crystallized from crystallized ethyl acetate to give the title compound (as pale yellow powder; 167 mg) having the following physical data.

NMR: δ 7.84(0.5H, s), 7.40~6.90(12.5H, m), 6.62(0.5H, d), 6.57(0.5H, d), 6.22(0.5H, t), 6.15(0.5H, t), 4.65(1H, s), 4.62(1H, s), 3.80(1.5H, s), 3.79(1.5H, s), 3.35(1H, d), 3.31 (1H, d), 2.83(1H, t), 2.74(1H, t), 2.50(1H, t), 2.31(1H, t), 1.85(1H, m). 1.72(1H, m).

EXAMPLE 19

[1-(2-((N,N-Diphenylamino) carbamoyl)-1E-ethylidene)-1,2,3,4-tetrahydronaphthalen-5-yl] oxyacetic acid

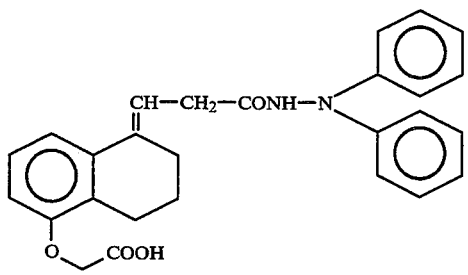

By the same procedure as example 2, using the compound prepared in example 18, the title compound having the following physical data.

NMR(DMSO): δ 10.58(1H, s), 7.40–6.80(12H, m), 6.67(1H, d), 6.15(1H, t), 4.61(2H, s), 3.18(2H, d), 2.68(2H, t), 2.45(2H, m), 1.74(2H, m);

IR(cm⁻¹): ν 3268, 2934, 1734, 1666, 1620, 1591, 1522, 1495, 1470, 1427, 1 31 8, 1239, 1179, 1127, 972, 885, 778, 749, 693, 633.

EXAMPLE 20

Methyl [1-(2E-((N,N-diphenylamino) carbamoyl)vinyl-1,2,3,4-tetrahydronaphthalen-5-yl] oxyacetate

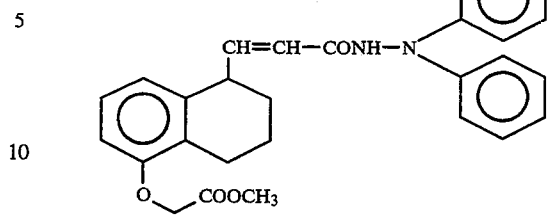

To a solution of the carboxylic acid (prepared in reference example 5, 150 mg) and catalytic amount of dimethylformamide in methylene chloride (5 ml) was added dropwise oxalyl chloride (2 ml) at 0° C. After stirred for 30 min at 0° C., the mixture was warmed up room temperature. After stirred for 30 min at room temperature, the mixture was concentrated under reduced pressure to give acyl chloride as a yellow oil. To a solution of the acyl chloride in pyridine (5 ml) was added 1,1-diphenylhydrazine hydrochloride (147 mg) at 0° C. After stirred for 30 min, the mixture was poured into 1N hydrochloric acid and extracted with methylene chloride. The extract was washed with a saturated aqueous solution of sodium chloride, dried over anhydrous magnesium sulfate, and evaporated. The residue was crystallized from ethyl acetate to give the title compound (as pale yellow powder; 200 mg) having the following physical data.

NMR: δ 7.60(0.5H, s), 7.40~7.05(11 H, m), 7.02(0.5H, t), 6.96(0.5H, t), 6.73(0.5H, d), 6.56(0.5H, d), 6.51 (0.5H, d), 6.48(0.5H, d), 6.31(0.5H, d), 5.70(1H, d), 4.64(1H, s), 4.62(1H, s), 3.80(1.5H, s), 3.78(1.5H, s), 3.67(0.5H, m), 3.56(0.5H, m), 2.90~2.60(2H, m), 2.00~1.60(4H, m).

EXAMPLE 21

[1-(2E-((N,N-Diphenylamino) carbamoyl)vinyl)-1,2,3,4-tetrahydronaphthalen-5-yl] oxyacetic acid

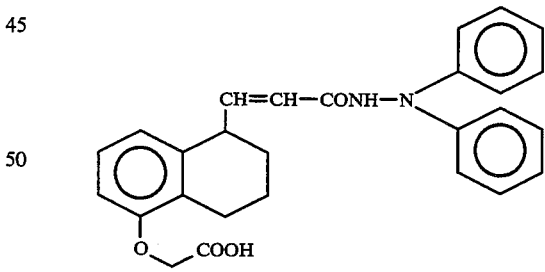

A solution of the methyl ester (prepared in example 20, 187 mg) in hydrochloric acid (2 ml) and acetic acid (2 ml) was stirred for 4 days at room temperature. The mixture was poured into water and extracted with methylene chloride-methanol (9:1). The extract was washed with a saturated aqueous solution of sodium chloride, dried over anhydrous magnesium sulfate, and evaporated. The residue was washed with ethyl acetate to give the title compound (pale blue powder, 164 mg) having the following physical data.

NMR(DMSO+D₂O): δ 7.40~7.10(4H, m), 7.10~6.50(10H, m), 5.82(1H, d), 4.58(2H, s), 3.65(1H, m), 2.63(2H, m), 2.00~1.40(4H, m);

IR(cm$^{-1}$): ν 3268, 3016, 2935, 1744, 1670, 1644, 1589, 1525, 1494, 1464, 1317, 1274, 1241, 1117, 1026, 986, 882, 779, 749, 692, 626.

EXAMPLE 22(a)~22(m)

By the same procedure as reference example 1→reference example 2→example 20 (using corresponding amine compound)→example 2, using methyl [1-(3-hydroxypropyl)-1,2,3,4-tetrahydronaphthalen-5-yl] oxyacetate, methyl [2-(2-hydroxyethyl)-1,2,3,4-tetrahydronaphthalen-5-Yl] oxyacetate or [1-(2-hydroxyethyl)-indan-4-yl] oxyacetate as starting materials, the compounds having the following physical data shown in the table 8 were given.

TABLE 8

| Ex. No. | Structure | TLC | IR (cm$^{-1}$) m.p. (°C.) |
|---|---|---|---|
| 22(a) | 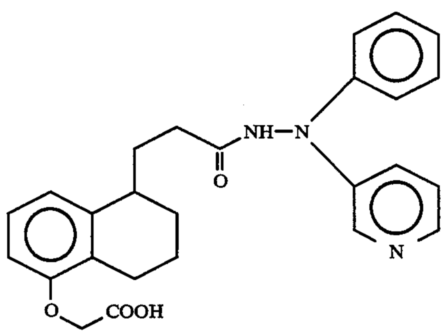 | Rf = 0.39 (CH$_3$OH:CHCl$_3$ = 3:7) | 182~184° C. |
| 22(b) | 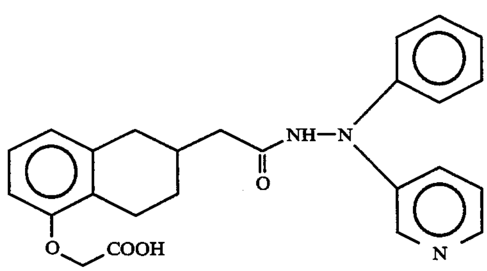 | Rf = 0.38 (CH$_3$OH:CHCl$_3$ = 3:7) | 250~251° C. |
| 22(c) | 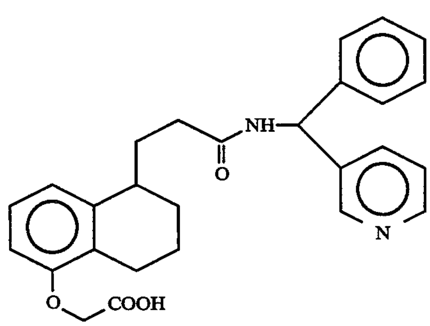 | Rf = 0.42 (CH$_3$OH:CHCl$_3$ = 3:7) | ν 3283, 2932, 1646, 1582, 1538, 1464, 1428, 1235, 1112, 756, 702. |
| 22(d) | 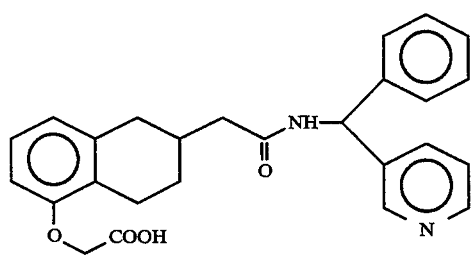 | Rf = 0.39 (CH$_3$OH:CHCl$_3$ = 3:7) | 215~218° C. |

TABLE 8-continued
| Ex. No. | Structure | TLC | IR (cm$^{-1}$) m.p. (°C.) |
|---|---|---|---|
| 22(e) | 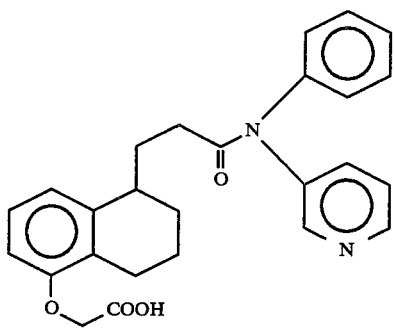 | Rf = 0.49 (CH$_3$OH:CHCl$_3$ = 3:7) | ν 3424, 2932, 1673, 1595, 1462, 1426, 1270, 1236, 1111, 757, 703. |
| 22(f) | 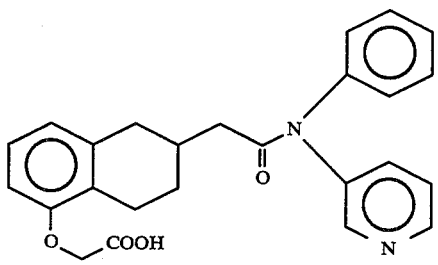 | Rf = 0.46 (CH$_3$OH:CHCl$_3$ = 3:7) | ν 3397, 2924, 1673, 1587, 1492, 1479, 1466, 1426, 1299, 1258, 1107, 763, 704. |
| 22(g) | 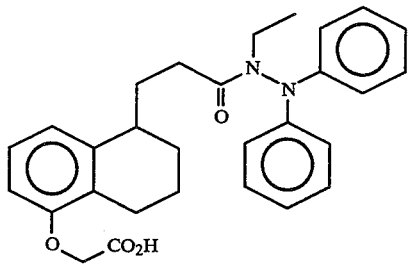 | Rf = 0.25 (MeOH:CH$_2$Cl$_2$ = 1:9) | ν 2933, 1737, 1666, 1589, 1494, 1462, 1411, 1331, 1273, 1118, 1077, 1030, 919, 887, 750, 694, 625, 499. |
| 22(h) | 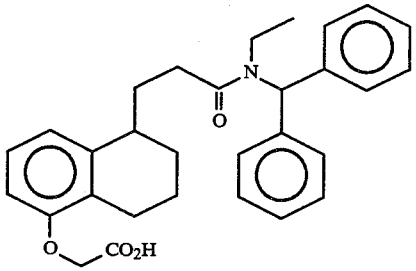 | Rf = 0.24 (MeOH:CH$_2$Cl$_2$ = 1:9) | ν 2933, 1737, 1580, 1496, 1463, 1377, 1341, 1207, 1118, 1077, 1031, 869, 812, 775, 755, 727, 701, 611. |
| 22(i) | 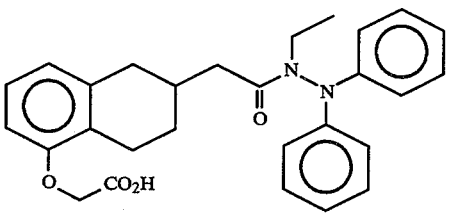 | Rf = 0.19 (MeOH:CH$_2$Cl$_2$ = 1:9) | ν 2927, 1737, 1666, 1629, 1589, 1466, 1494, 1407, 1377, 1274, 1118, 1031, 751, 695, 625, 503. |

TABLE 8-continued

| Ex. No. | Structure | TLC | IR (cm$^{-1}$) m.p. (°C.) |
|---|---|---|---|
| 22(j) | 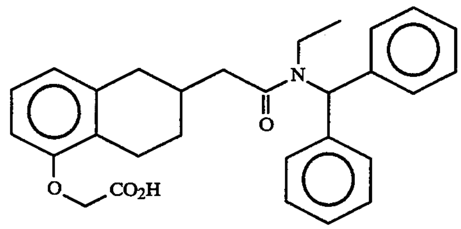 | Rf = 0.17 (MeOH:CH$_2$Cl$_2$ = 1:9) | ν 3030, 2932, 1737, 1585, 1496, 1466, 1377, 1345, 1244, 1208, 1118, 870, 813, 766, 734, 702, 640. |
| 22(k) | 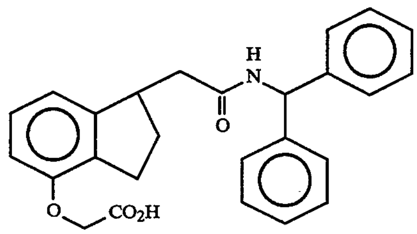 | Rf = 0.30 (CHCl$_3$:MeOH = 7:3) | ν 3258, 3062, 2953, 1725, 1639, 1591, 1541, 1494, 1478. |
| 22(l) | 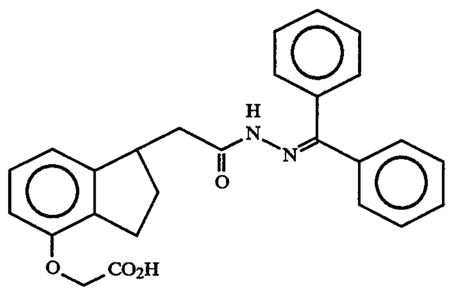 | Rf = 0.35 (CHCl$_3$:MeOH = 7:3) | ν 3152, 3062, 2945, 1713, 1642, 1608, 1589, 1477, 1448, 1392, 1272. |
| 22(m) | 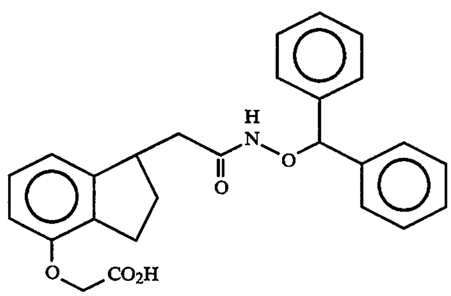 | Rf = 0.32 (CHCl$_3$:MeOH = 7:3) | ν 3217, 3029, 2937, 1640, 1588, 1495, 1475, 1454, 1433. |

The compounds shown in the table 8 are named as follows

22(a) [1-(2-(N-Phenyl-N-(3-pyridyl) amino) amino carbonylethyl)-1,2,3,4-tetrahydronaphthalen-5-yl] oxyacetic acid 22(b) [2-((N-Phenyl-N-(3-pyridyl) amino) aminocarbonylmethyl)-1,2,3,4-tetrahydronaphthalen-5-yl] oxyacetic acid 22(c) [1-(2-(1-Phenyl-1-(3-pyridyl) methyl) aminocarbonylethyl)-1,2,3,4-tetrahydronaphthalen-5-yl] oxyacetic acid 22(d) [2-((1-Phenyl-1-(3-pyridyl) methyl) aminocarbonylmethyl)-1,2,3,4-tetrahydronaphthalen-5-yl] oxyacetic acid 22(e) [1-(2-(N-Phenyl-N-(3-pyridyl) amino) carbonylethyl)-1,2,3,4-tetrahydronaphthalen-5-yl] oxyacetic acid 22(f) [2-((N-Phenyl-N-(3-pyridyl) amino) carbonylmethyl)-1,2,3,4-tetrahydronaphthalen-5-yl] oxyacetic acid 22(g) [1-(2-(N-Ethyl-N-(diphenylamino) amino) carbonylethyl)-1,2,3,4-tetrahydronaphthalen-5-yl] oxyacetic acid 22(h) [1-(2-(N-Ethyl-N-diphenylmethylamino) carbonylethyl)-1,2,3,4-tetrahydronaphthalen-5-yl] oxyacetic acid 22(i) [2-((N-Ethyl-N-(diphenylamino) amino) carbonylmethyl)-1,2,3,4-tetrahydronaphthalen-5-yl] oxyacetic acid 22(j) [2-((N-Ethyl-N-diphenylmethylamino) carbonylmethyl)-1,2,3,4-tetrahydronaphthalen-5-yl] oxyacetic acid 22(k) [1-(Diphenylmethylaminocarbonylmethyl)-indan-4-yl] oxyacetic acid 22(l) [1-((Diphenylmethylideneamino) aminocarbonylmethyl)-indan-4-yl] oxyacetic acid 22(m) [1-(Diphenylmethoxyaminocarbonylmethyl)-indan-4-yl] oxyacetic acid

EXAMPLE 23

[1-((N-Phenyl-N-(3-pyridyl) amino) carbomoyl)-3,4-dihydronaphthalen-5-yl] oxyacetic acid

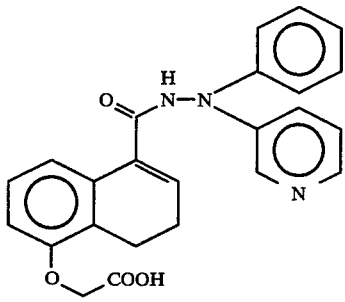

By the same procedure as reference example 2→example 20 (using N-phenyl-N-pyridylhydrazine)→example 2, using methyl (1-formyl-3,4-dihydronaphthalen-5-yl) oxyacetate as starting material, the title compound having the following physical data was given.

NMR(DMSO+D$_2$O): δ 8.5~6.5(13H, m), 2.85(2H, brt), 2.60~2.40(2H, m).

FORMULATION EXAMPLE 1

The following components were admixed in conventional method and punched out to obtain 100 tablets each containing 5 mg of active ingredient.

| | |
|---|---|
| [1-(2-(N,N-Diphenylamino)aminocarbonylethyl)-1,2,3,4-tetrahydronaphthalen-5-yl] oxyacetic acid | 500 mg |
| Carboxymethylcellulose calcium | 200 mg |
| Magnesium stearate | 100 mg |
| Microcrystalline cellulose | 9.2 g |

FORMULATION EXAMPLE 2

The following components were admixed in conventional manner. The solution was sterilized in conventional manner, placed 5 ml portion into 10 ml ampoules and freeze-dried to obtain 100 ampoules each containing 2 mg of the active ingredient.

| | |
|---|---|
| [1-(2-(N,N-Diphenylamino)aminocarbonylethyl)-1,2,3,4-tetrahydronaphthalen-5-yl] oxyacetic acid | 200 mg |
| Citric acid, anhydrous | 20 mg |
| Distilled water | 500 ml |

"While the invention has been described in detail and with reference to specific examples thereof, it will be apparent to one skilled in the art that various changes and modifications can be made therein without departing from the spirit and scope thereof."

What we claim is:

1. A fused benzeneoxyacetic acid derivative of the formula (1):

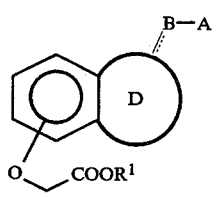
(I)

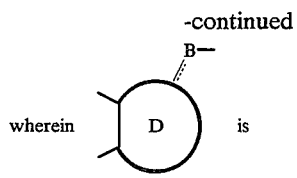

wherein D is

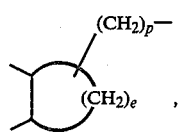
(i)

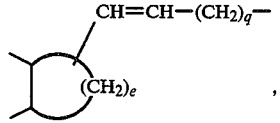
(ii)

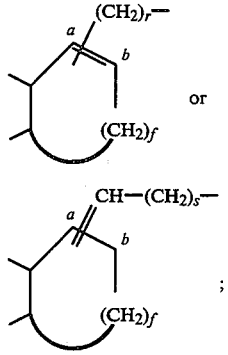

A is —COW;
W is
  (i) —NR$^2$R$^3$,
  (ii) —NR$^4$—OR$^5$,
  (iii) —NR$^4$—NR$^2$R$^3$ or
  (iv) —NR$^4$—N=Cr$^2$R$^3$;
R$^1$ is a hydrogen atom or C$_{1-4}$ alkyl;
R$^2$ and R$^3$ each, independently, is
  (i) a hydrogen atom
  (ii) phenyl,
  (iii) benzoylphenyl,
  (iv) a 4–7 membered, unsaturated monocyclic hetero ring containing one nitrogen atom as a hetero atom or
  (v) C$_{1-4}$ alkyl substituted by (1) 1 to 3 of phenyl or (2) one phenyl and one 4–7 membered, unsaturated monocyclic hetero ring containing one nitrogen atom as a hetero atom;
R$^4$ is a hydrogen atom, C$_{1-6}$ alkyl or phenyl;
R$^5$ is
  (i) phenyl,
  (ii) a 4–7 membered, unsaturated monocyclic hetero ring containing one nitrogen atom as hetero atom or
  (iii) C$_{1-4}$ alkyl substituted by (1) 1 to 3 of phenyl or (2) one phenyl and one 4–7 membered, unsaturated monocyclic hetero ring containing one nitrogen atom as a hetero atom;
the said phenyl and hetero rings may be also substituted by C$_{1-4}$ alkyl, C$_{1-4}$ alkoxy, a halogen atom, nitro or trihalomethyl, when R$^2$, R$^3$, R$^4$ or R$^5$ is phenyl or the group containing phenyl, or when R$^2$, R$^3$ or R$^5$ is said hetero ring or the group containing the hetero ring;

e is 3–5;
f is 1–3;
p is 0–4;
q is 0–2;
r is 0–4;
s is 0–3;
with the proviso that, when

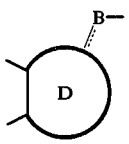

is the formula (iii) or (iv), —(CH$_2$)$_r$ or =CH—(CH$_2$)$_s$ in the side chain is bonded to the carbon atom at the position a or b in the ring;

or non-toxic salts thereof or non-toxic acid addition salts thereof.

2. A compound according to claim 1, wherein R$^1$ is a hydrogen atom.

3. A compound according to claim 1, wherein R$^1$ is C$_{1-4}$ alkyl.

4. A compound according to claim 1, wherein

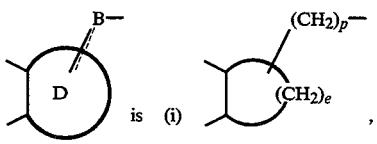

in which p and e have the same meaning as defined in claim 1.

5. A compound according to claim 1, wherein

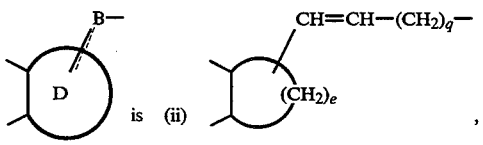

in which q and e have the same meaning as defined in claim 1.

6. A compound according to claim 1, wherein

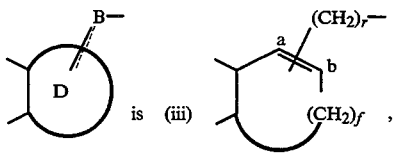

in which r, f, a and b have the same meaning as defined in claim 1.

7. A compound according to claim 1, wherein

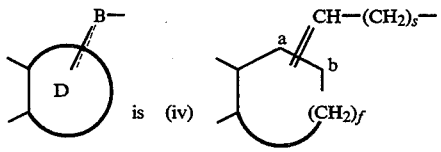

in which s, f a and b have the same meaning as defined in claim 1.

8. A compound according to claim 1, wherein R$^2$ and R$^3$ each, independently, is
  (i) a hydrogen atom,
  (ii) phenyl,
  (iii) benzoylphenyl,
  (iv) a 7 membered, unsaturated monocyclic hetero ring containing one nitrogen atom as a hetero atom or
  (v) C$_{1-4}$ alkyl substituted by (1) 1 to 3 of phenyl or (2) one phenyl and one 7 membered, unsaturated monocyclic hetero ring containing one nitrogen atom as a hetero atom;
with the proviso that at least one of R$^2$ and R$^3$ is the group containing the hetero ring as defined above.

9. A compound according to claim 1, wherein R$^2$ and R$^3$ each, independently, is
  (i) a hydrogen atom,
  (ii) phenyl,
  (iii) benzoylphenyl,
  (iv) a 6 membered, unsaturated monocyclic hetero ring containing one nitrogen atom as a hetero atom or
  (v) C$_{1-4}$ alkyl substituted by (1) 1 to 3 or phenyl or (2) one phenyl and one 6 membered, unsaturated monocyclic hetero ring containing one nitrogen atom as a hetero atom;
with the proviso that at least one of R$^2$ and R$^3$ is the group containing the hetero ring as defined above.

10. A compound according to claim 1, wherein R$^2$ and R$^3$ each, independently, is
  (i) a hydrogen atom,
  (ii) phenyl,
  (iii) benzoylphenyl,
  (iv) a 4 or 5 membered, unsaturated monocyclic hetero ring containing one nitrogen atom as a hetero atom or
  (v) C$_{1-4}$ alkyl substituted by (1) 1 to 3 of phenyl or (2) one phenyl and one 4 or 5 membered, unsaturated monocyclic hetero ring containing one nitrogen atom as a hetero atom;
with the proviso that at least one of R$^2$ and R$^3$ is the group containing the hetero ring as defined above.

11. A compound according to claim 1, wherein R$^2$ and R$^3$ each, independently, is
  (i) hydrogen atom,
  (ii) phenyl,
  (iii) benzoylphenyl or
  (iv) C$_{1-4}$ alkyl substituted by 1 to 3 of phenyl.

12. A compound according to claim 8, which is
[1-(2-(N-Phenyl-N-(3-azepinyl) aminocarbonyl) ethyl)-1,2,3,4-tetrahydronaphthalen-5-yl] oxyacetic acid,
[1-(2E-((1-(3-Azepinyl)-1-phenylmethyl)aminocarbonyl)vinyl-1,2,3,4-tetrahydronaphthalen-5-yl] oxyacetic acid,
[1-(2-((1-(3-Azepinyl)-1-phenylmethyl)aminocarbonyl)ethyl)-3,4-dihydronaphthalen-5-yl] oxyacetic acid or
[1-(2-((1-(3-Azepinyl)-1-phenylmethyl)aminocarbonyl)-1E-ethylidene)-1,2,3,4-tetrahydronaphthalen-5-yl] oxyacetic acid.

13. A compound according to claim 10, which is
[1-(2-(N-Phenyl-N-(3-pyrrolyl) aminocarbonyl) ethyl)-1,2,3,4-tetrahydronaphthalen-5-yl] oxyacetic acid,
[1-(2E-((1-(3-Pyrrolyl)-1-phenylmethyl)aminocarbonyl)vinyl-1,2,3,4-tetrahydronaphthalen-5-yl] oxyacetic acid,

[1-(2-((1-(3-Pyrrolyl)-1-phenylmethyl)aminocarbonyl)ethyl)-3,4-dihydronaphthalen-5-yl] oxyacetic acid or

[1-(2-((1-(3-Pyrrolyl)-1-phenylmethyl)aminocarbonyl)-1E-ethylidene)-1,2,3,4-tetrahydronaphthalen-5-yl] oxyacetic acid.

14. A pharmaceutical composition which comprises, as active ingredient, an effective amount of a fused benzeneoxyacetic acid derivative of the formula (I) depicted in claim 1 or a non-toxic salt thereof, or a non-toxic acid addition salt thereof, with a pharmaceutical carrier or coating.

15. A method for the prevention and/or the treatment of thrombosis, arteriosclerosis, ischemic heart diseases, gastric ulcer or hypertention, which comprises the administration of an effective amount of a fused benzeneoxyacetic acid derivative of the formula (I) depicted in claim 1 or a non-toxic salt thereof, or a non-toxic acid addition salt thereof.

16. A compound according to claim 9, which is
[1-(2-(N-Phenyl-N-(1-(3-pyridyl)-1-phenylmethyl) aminocarbonyl)ethyl)-1,2,3,4-tetrahydronaphthalen-5-yl] oxyacetic acid,
[1-(2-((1-(3-Pyridyl)-1-phenylmethoxy) aminocarbonyl) ethyl)-1,2,3,4-tetrahydronaphthalen-5-yl] oxyacetic acid,
[1-(2-(N-Propyl-N-(1-(3-pyridyl)-1-phenylmethoxy) aminocarbonyl) ethyl)-1,2,3,4-tetrahydronaphthalen-5-yl] oxyacetic acid,
[1-(2-((1-(3-Pyridyl)-1-phenylmethylamino)aminocarbonyl)ethyl)-1,2,3,4-tetrahydronaphthalen-5-yl] oxyacetic acid,
[1-(2-(N-Propyl-N-(1-(3-pyridyl)-1-phenylmethylideneamino) aminocarbonyl) ethyl)-1,2,3,4-tetrahydronaphthalen-5-yl] oxyacetic acid,
[1-(2-((1,1-Di(3-pyridyl)methyl) aminocarbonyl) ethyl)-1,2,3,4-tetrahydronaphthalen-5-yl] oxyacetic acid,
[1-(2E-((1-(3-Pyridyl)-1-phenylmethyl) aminocarbonyl) vinyl-1,2,3,4-tetrahydronaphthalen-5-yl] oxyacetic acid,
[1-(2E-((1,1-Di(3-pyridyl) methyl) aminocarbonyl) vinyl-1,2,3,4-tetrahydronaphthalen-5-yl] oxyacetic acid,
[1-(2-((1,1-Di(3-pyridyl) methyl) aminocarbonyl) ethyl)-3,4-dihydronaphthalen-5-yl] oxyacetic acid,
[1-(2-((1-(3-Pryidyl)-1-phenylmethyl) aminocarbonyl)-1E-ethylidene)-1,2,3,4-tetrahydronaphthalen-5-yl] oxyacetic acid,
[1-(2-((1,1-Di(3-pyridyl) methyl) aminocarbonyl)-1E-ethylidene)-1,2,3,4-tetrahydronaphthalen-5-yl] oxyacetic acid,
[1-(2-(1-(3-Pyridyl)-1-phenylmethyl) aminocarbonylethyl)-1,2,3,4-tetrahydronaphthalen-5yl] oxyacetic acid,
[1-(2-(N-Phenyl-N-(3-pyridyl) amino) aminocarbonylethyl)-1,2,3,4-tetrahydronaphthalen-5-yl] oxyacetic acid,
[2-((N-Phenyl-N-(3-pyridyl) amino) aminocarbonylmethyl)-1,2,3,4-tetrahydronaphthalen-5-yl] oxyacetic acid,
[1-(2-(1-Phenyl-1-(3-pyridyl) methyl) aminocarbonylethyl)-1,2,3,4-tetrahydronaphthalen-5-yl] oxyacetic acid,
[2-((1-Phenyl-1-(3-pyridyl) methyl) aminocarbonylmethyl)-1,2,3,4-tetrahydronaphthalen-5-yl] oxyacetic acid,
[1-(2-(N-Phenyl-N-(3-pyridyl) amino) carbonylethyl)-1,2,3,4-tetrahydronaphthalen-5-yl] oxyacetic acid, or
[2-((N-Phenyl-N-(3-pyridyl) amino) carbonylmethyl)-1,2,3,4-tetrahydronaphthalen-5-yl] oxyacetic acid.

17. A compound according to claim 11, which is
[1-(2-((N,N-Diphenylamino) aminocarbonyl) ethyl) benzocycloheptan-6-yl] oxyacetic acid,
[1-(2E-((N,N-Diphenylamino) aminocarbonyl) vinyl)-indan-4-yl] oxyacetic acid,
[1-(2-((N,N-Diphenylamino) aminocarbonyl)-1E-ethylidene)-indan-4-yl] oxyacetic acid,
[2-(2-((N,N-Diphenylamino) aminocarbonyl) ethyl)-3H-inden-4-yl] oxyacetic acid,
[1-(2-((N,N-Diphenylamino) aminocarbonyl) ethyl)-1,2,3,4-tetrahydronaphthalen-6-yl] oxyacetic acid,
[1-(2-(N-Phenyl-N-(diphenylmethyl) aminocarbonyl) ethyl)-1,2,3,4-tetrahydronaphthalen-5-yl] oxyacetic acid,
[1-(2-(N-Phenyl-N-(amino) aminocarbonyl) ethyl)-1,2,3,4-tetrahydronaphthalen-5-yl] oxyacetic acid,
[1-(2-((Diphenylmethyl) aminocarbonyl) ethyl)-3,4-dihydronaphthalen-5-yl] oxyacetic acid,
(1-Dibenzylaminocarbonyl-1,2,3,4-tetrahydronaphthalen-5-yl) oxyacetic acid,
[1-(2-Benzoylphenylaminocarbonyl)-1,2,3,4-tetrahydronaphthalen-5-yl] oxyacetic acid,
[1-(Diphenylmethylaminocarbonyl)-1,2,3,4-tetrahydronaphthalen-5-yl] oxyacetic acid,
[1-((N,N-Diphenylamino) aminocarbonyl)-1,2,3,4-tetrahydronaphthalen-5-yl] oxyacetic acid,
[1-((1,2-Diphenylethyl) aminocarbonyl)-1,2,3,4-tetrahydronaphthalen-5-yl] oxyacetic acid,
[1-((2,2-Diphenylethyl) aminocarbonyl)-1,2,3,4-tetrahyronaphthalen-5-yl] oxyacetic acid,
[1-(Diphenylmethoxyaminocarbonyl)-1,2,3,4-tetrahydronaphthalen-5-yl] oxyacetic acid,
[1-((Diphenylmethlideneamino) aminocarbonyl)-1,2,3,4-tetrahydronaphthalen-5-yl] oxyacetic acid,
[1-((3,3-Diphenylpropyl)aminocarbonyl)-1,2,3,4-tetrahydronaphthalen-5-yl] oxyacetic acid,
[1-(2-Diphenylaminocarbonylethyl)-1,2,3,4-tetrahydronaphthalen-5-yl] oxyacetic acid,
[2-(Diphenylmethoxyaminocarbonylmethyl)-1,2,3,4-tetrahydronaphthalen-5-yl] oxyacetic acid,
[2-((Diphenylmethylideneamino)aminocarbonylmethyl)-1,2,3,4-tetrahydronaphthalen-5-yl] oxyacetic acid,
[2-((2,2-Diphenylethyl) aminocarbonylmethyl)-1,2,3,4-tetrahydronaphthalen-5-yl] oxyacetic acid,
[2-((3,3-Diphenylpropyl) aminocarbonylmethyl)-1,2,3,4-tetrahydronaphthalen-5-yl] oxyacetic acid,
[1-(Diphenylmethoxyaminocarbonylmethyl)-1,2,3,4-tetrahydronaphthalen-5-yl] oxyacetic acid,
[1-((N-Benzyl-N-phenylamino) carbonylmethyl-1,2,3,4-tetrahydronaphthalen-5-yl] oxyacetic acid,
[1-(Dibenzylaminocarbonylmethyl)-1,2,3,4-tetrahydronaphthalen-5-yl] oxyacetic acid,
[1-((2-Benzoylphenyl) aminocarbonylmethyl)-1,2,3,4-tetrahydronaphthalen-5-yl] oxyacetic acid,
[1-(Diphenylmethylaminocarbonylmethyl)-1,2,3,4-tetrahydronaphthalen-5-yl] oxyacetic acid,
[1-((N,N-Diphenylamino) aminocarbonylmethyl)-1,2,3,4-tetrahydronaphthalen-5-yl] oxyacetic acid,
[1-((1,2-Diphenylethyl) aminocarbonylmethyl)-1,2,3,4-tetrahydronaphthalen-5-yl] oxyacetic acid,

[1-(2-(N-Benzyl-N-phenylamino) carbonylethyl)-1,2,3,4-tetrahydronaphthalen-5-yl] oxyacetic acid,

[1-(2-Dibenzylaminocarbonylethyl)-1,2,3,4-tetrahydronaphthalen-5-yl] oxyacetic acid,

[1-(2-(2-Benzoylphenyl) aminocarbonylethyl)-1,2,3,4-tetrahydronaphthalen-5-yl] oxyacetic acid,

[1-(2-Diphenylmethylaminocarbonylethyl)-1,2,3,4-tetrahydronaphthalen-5-yl] oxyacetic acid,

[1-(2-(N,N-Diphenylamino) aminocarbonylethyl)-1,2,3,4-tetrahydronaphthalen-5-yl] oxyacetic acid,

[1-(2-(1,2-Diphenylethyl) aminocarbonylethyl)-1,2,3,4-tetrahydronaphthalen-5-yl] oxyacetic acid,

[1-(2-(2,2-Diphenylethyl) aminocarbonylethyl)-1,2,3,4-tetrahydronaphthalen-5-yl] oxyacetic acid,

[1-(2-Diphenylmethoxyaminocarbonylethyl)-1,2,3,4-tetrahydronaphthalen-5-yl] oxyacetic acid,

[1-(2-(Diphenylmethylideneamino) aminocarbonylethyl)-1,2,3,4-tetrahydronaphthalen-5-yl] oxyacetic acid,

[1-(2-(3,3-Diphenylpropyl) aminocarbonylethyl)-1,2,3,4-tetrahydronaphthalen-5-yl] oxyacetic acid,

[2-(Diphenylmethylaminocarbonylmethyl-1,2,3,4-tetrahydronaphthalen-5-yl] oxyacetic acid,

[2-((N,N-Diphenylamino) aminocarbonylmethyl)-1,2,3,4-tetrahydronaphthalen-5-yl] oxyacetic acid,

[2-(2-(N,N-dibenzylamino) carbonylethyl)-1,2,3,4-tetrahydronaphthalen-5-yl] oxyacetic acid,

[2-(2(Diphenylmethylamino) carbonylethyl)-1,2,3,4-tetrahydronaphthalen-5-yl] oxyacetic acid,

[2-(2-(N,N-Diphenylamino) aminocarbonylethyl)-1,2,3,4-tetrahydronaphthalen-5-yl] oxyacetic acid,

[2-(2-(Diphenylmethylideneamino) aminocarbonylethyl)-1,2,3,4-tetrahydronaphthalen-5-yl] oxyacetic acid,

[1-(3-(N,N-dibenzylamino) carbonylpropyl)-1,2,3,4-tetrahydronaphthalen-5-yl] oxyacetic acid,

[1-(3-Diphenylmethylaminocarbonylpropyl)-1,2,3,4-tetrahydronaphthalen-5-yl] oxyacetic acid,

[1-(3-(N,N-Diphenylamino) carbonylpropyl)-1,2,3,4-tetrahydronaphthalen-5-yl] oxyacetic acid,

[1-(2-Bis(4-methylphenyl) methylaminocarbonylethyl)-1,2,3,4-tetrahydronaphthalen-5-yl] oxyacetic acid,

[1-(2-Bis(4-methoxyphenyl) methylaminocarbonylethyl)-1,2,3,4-tetrahydronaphthalen-5-yl] oxyacetic acid,

[1-(2-Bis(4-chlorophenyl) methylaminocarbonylethyl)-1,2,3,4-tetrahydronaphthalen-5-yl] oxyacetic acid,

[1-(2-(1-(4-Nitrophenyl)-1-phenylmethyl) aminocarbonylethyl)-1,2,3,4-tetrahydronaphthalen-5-yl] oxyacetic acid,

[1-((Diphenylmethylideneamino) aminocarbonylmethyl)-1,2,3,4-tetrahydronaphthalen-5-yl] oxyacetic acid,

[1-((2,2-diphenylethyl) aminocarbonylmethyl)-1,2,3,4-tetrahydronaphthalen-5-yl] oxyacetic acid,

[1-((3,3-Diphenylpropyl) aminocarbonylmethyl)-1,2,3,4-tetrahydronaphthalen-5-yl] oxyacetic acid,

[1-(3-(N,N-Diphenylamino) aminocarbonylpropyl)-1,2,3,4-tetrahydronaphthalen-5-yl] oxyacetic acid,

[2-(Diphenylmethylaminocarbonyl)-1,2,3,4-tetrahydronaphthalen-5-yl] oxyacetic acid,

[2-((N,N-Diphenylamino) aminocarbonyl-1,2,3,4-tetrahydronaphthalen-5-yl] oxyacetic acid,

[2-(Diphenylmethoxyaminocarbonyl)-1,2,3,4-tetrahydronaphthalen-5-yl] oxyacetic acid,

[2-((Diphenylmethlideneamino) aminocarbonyl)-1,2,3,4-tetrahydronaphthalen-5-yl] oxyacetic acid,

[2-((2,2-diphenylethyl) aminocarbonyl)-1,2,3,4-tetrahydronaphthalen-5-yl] oxyacetic acid,

[2-((N,N-Dibenzylamino) carbonylmethyl)-1,2,3,4-tetrahydronaphthalen-5-yl] oxyacetic acid,

[1-(2-(N-Ethyl-N-(diphenylamino) amino) carbonylethyl)-1,2,3,4-tetrahydronaphthalen-5-yl] oxyacetic acid,

[1-(2-(N-Ethyl-N-diphenylmethylamino) carbonylethyl)-1,2,3,4-tetrahydronaphthalen-5-yl] oxyacetic acid,

[2-((N-Ethyl-N-(diphenylamino) amino) carbonylmethyl)-1,2,3,4-tetrahydronaphthalen-5-yl] oxyacetic acid,

[2-((N-Ethyl-N-diphenylmethylamino) carbonylmethyl)-1,2,3,4-tetrahydronaphthalen-5-yl] oxyacetic acid,

[1-(Diphenylmethylaminocarbonylmethyl)-indan-4-yl] oxyacetic acid,

[1-((Diphenylmethylideneamino) aminocarbonylmethyl)-indan-4-yl] oxyacetic acid or

[1-(Diphenylmethoxyaminocarbonylmethyl)-indan-4-yl] oxyacetic acid.

18. A compound recited in claim 19, wherein said compound is [1-(2-(N,N-Diphenylamino)aminocarbonylethyl)-1,2,3,4-tetrahydronaphthalen-5-yl] oxyacetic acid.

* * * * *